US010548707B2

(12) United States Patent
Zaver et al.

(10) Patent No.: US 10,548,707 B2
(45) Date of Patent: Feb. 4, 2020

(54) EMBOLIC PROTECTION DEVICES HAVING RADIOPAQUE ELEMENTS

(71) Applicant: Covidien LP, Mansfield, MA (US)

(72) Inventors: Steven Zaver, Plymouth, MN (US); Sengkham Sirivong, Big Lake, MN (US); Christopher Quinn, Minneapolis, MN (US); Earl Slee, Laguna Niguel, CA (US); Linda Anderson, Andover, MN (US)

(73) Assignee: Covidien LP, Mansfield, MA (US)

( * ) Notice: Subject to any disclaimer, the term of this patent is extended or adjusted under 35 U.S.C. 154(b) by 779 days.

(21) Appl. No.: 14/714,488

(22) Filed: May 18, 2015

(65) Prior Publication Data
US 2015/0327977 A1 Nov. 19, 2015

Related U.S. Application Data

(63) Continuation of application No. 11/729,324, filed on Mar. 28, 2007, now Pat. No. 9,089,404.
(Continued)

(51) Int. Cl.
*A61F 2/01* (2006.01)

(52) U.S. Cl.
CPC ............... *A61F 2/013* (2013.01); *A61F 2/01* (2013.01); *A61F 2002/018* (2013.01);
(Continued)

(58) Field of Classification Search
CPC ... A61B 2090/3966; A61B 90/39; A61F 2/01; A61F 2/013; A61F 2002/018; A61F 2002/016; A61F 2250/0098
See application file for complete search history.

(56) References Cited

U.S. PATENT DOCUMENTS 4,572,186 A 2/1986 Gould et al.
4,681,110 A 7/1987 Wiktor
(Continued)

FOREIGN PATENT DOCUMENTS

EP 0838230 A2 4/1998
WO 2004030574 A1 4/2004

OTHER PUBLICATIONS

Invitation to Pay Additional Fees and Partial International Search Report from counterpart International Application No. PCT/US2007/007733, dated Aug. 16, 2007, 8 pp.
(Continued)

*Primary Examiner* — Alexander J Orkin

(57) ABSTRACT

A device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a discontinuous loop extending around a portion of a perimeter of the proximal facing opening, the discontinuous loop having a gap and the gap being proximate to the elongate support member.

21 Claims, 20 Drawing Sheets

Related U.S. Application Data

(60) Provisional application No. 60/831,751, filed on Jul. 19, 2006, provisional application No. 60/800,147, filed on May 12, 2006, provisional application No. 60/788,255, filed on Mar. 31, 2006.

(52) U.S. Cl.
CPC ............... *A61F 2230/0008* (2013.01); *A61F 2230/0067* (2013.01); *A61F 2250/0098* (2013.01)

(56) References Cited

U.S. PATENT DOCUMENTS

| | | | |
|---|---|---|---|
| 4,733,665 A | 3/1988 | Palmaz |
| 4,776,337 A | 10/1988 | Palmaz |
| 4,960,410 A | 10/1990 | Pinchuk |
| 5,341,818 A | 8/1994 | Abrams et al. |
| 5,573,520 A | 11/1996 | Schwartz et al. |
| 5,628,788 A | 5/1997 | Pinchuk |
| 5,639,278 A | 6/1997 | Dereume et al. |
| 5,746,701 A | 5/1998 | Noone |
| 5,824,042 A | 10/1998 | Lombardi et al. |
| 5,980,471 A | 11/1999 | Jafari |
| 6,001,068 A | 12/1999 | Uchino et al. |
| 6,048,338 A | 4/2000 | Larson et al. |
| 6,066,149 A | 5/2000 | Samson et al. |
| 6,102,890 A | 8/2000 | Stivland et al. |
| 6,129,739 A | 10/2000 | Khosravi |
| 6,165,213 A | 12/2000 | Goicoechea et al. |
| 6,174,330 B1 | 1/2001 | Stinson |
| 6,245,087 B1 | 6/2001 | Addis |
| 6,248,082 B1 | 6/2001 | Jafari |
| 6,251,135 B1 | 6/2001 | Stinson et al. |
| 6,325,815 B1 | 12/2001 | Kusleika et al. |
| 6,325,826 B1 | 12/2001 | Vardi et al. |
| 6,334,871 B1 | 1/2002 | Dor et al. |
| 6,340,367 B1 | 1/2002 | Stinson et al. |
| 6,340,368 B1 | 1/2002 | Verbeck |
| 6,355,051 B1 | 3/2002 | Sisskind et al. |
| 6,402,772 B1 | 6/2002 | Amplatz et al. |
| 6,468,301 B1 | 10/2002 | Amplatz et al. |
| 6,494,895 B2 | 12/2002 | Addis |
| 6,530,939 B1 | 3/2003 | Hopkins et al. |
| 6,544,197 B2 | 4/2003 | DeMello |
| 6,544,279 B1 | 4/2003 | Hopkins et al. |
| 6,592,570 B2 | 7/2003 | Abrams et al. |
| 6,602,208 B2 | 8/2003 | Jafari |
| 6,602,228 B2 | 8/2003 | Nanis et al. |
| 6,626,936 B2 | 9/2003 | Stinson |
| 6,660,021 B1 | 12/2003 | Palmer et al. |
| 6,663,652 B2 | 12/2003 | Daniel et al. |
| 6,740,061 B1 | 5/2004 | Oslund et al. |
| 6,814,746 B2 | 11/2004 | Thompson et al. |
| 6,866,642 B2 | 3/2005 | Kellerman et al. |
| 6,878,291 B2 | 4/2005 | Lowe et al. |
| 6,893,451 B2 | 5/2005 | Cano et al. |
| 6,918,882 B2 | 7/2005 | Skujins et al. |
| 6,932,837 B2 | 8/2005 | Amplatz et al. |
| 6,955,685 B2 | 10/2005 | Escamilla et al. |
| 6,964,672 B2 | 11/2005 | Brady et al. |
| 6,969,396 B2 | 11/2005 | Krolik et al. |
| 7,220,271 B2 | 5/2007 | Clubb et al. |
| 8,152,833 B2 | 4/2012 | Zaver et al. |
| 9,089,404 B2 | 7/2015 | Zaver et al. |
| 2002/0029061 A1 | 3/2002 | Amplatz et al. |
| 2002/0143361 A1 | 10/2002 | Douk et al. |
| 2002/0188314 A1 | 12/2002 | Anderson et al. |
| 2003/0023299 A1 | 1/2003 | Amplatz et al. |
| 2003/0069521 A1 | 4/2003 | Reynolds et al. |
| 2003/0176884 A1 | 9/2003 | Berrada et al. |
| 2003/0187495 A1 | 10/2003 | Cully et al. |
| 2003/0212429 A1 | 11/2003 | Keegan et al. |
| 2003/0212430 A1 | 11/2003 | Bose et al. |
| 2004/0024416 A1 | 2/2004 | Yodfat et al. |
| 2004/0153118 A1 | 8/2004 | Clubb et al. |
| 2004/0167567 A1 | 8/2004 | Cano et al. |
| 2004/0172055 A1 | 9/2004 | Huter et al. |
| 2004/0193208 A1 | 9/2004 | Talpade et al. |
| 2004/0204737 A1 | 10/2004 | Boismier et al. |
| 2004/0220608 A1 | 11/2004 | D'Aquanni et al. |
| 2004/0260331 A1 | 12/2004 | D'Aquanni et al. |
| 2005/0004595 A1 | 1/2005 | Boyle et al. |
| 2005/0038447 A1 | 2/2005 | Huffmaster |
| 2005/0096692 A1* | 5/2005 | Linder ............... A61F 2/013 606/200 |
| 2005/0101989 A1 | 5/2005 | Cully et al. |
| 2005/0126979 A1 | 6/2005 | Lowe et al. |
| 2005/0131449 A1 | 6/2005 | Salahieh et al. |
| 2005/0149111 A1 | 7/2005 | Kanazawa et al. |
| 2005/0177131 A1 | 8/2005 | Lentz et al. |
| 2005/0177132 A1 | 8/2005 | Lentz et al. |
| 2005/0177186 A1 | 8/2005 | Cully et al. |
| 2005/0192620 A1 | 9/2005 | Cully et al. |
| 2006/0030878 A1 | 2/2006 | Anderson et al. |
| 2006/0241681 A1* | 10/2006 | Brady ............... A61F 2/013 606/200 |

OTHER PUBLICATIONS

International Search Report and the Written Opinion from counterpart International Application No. PCT/US2007/007733, dated Nov. 28, 2007, 20 pp.

Prosecution History from U.S. Pat. No. 9,089,404, dated May 18, 2009 through Mar. 25, 2015, 189 pp.

\* cited by examiner

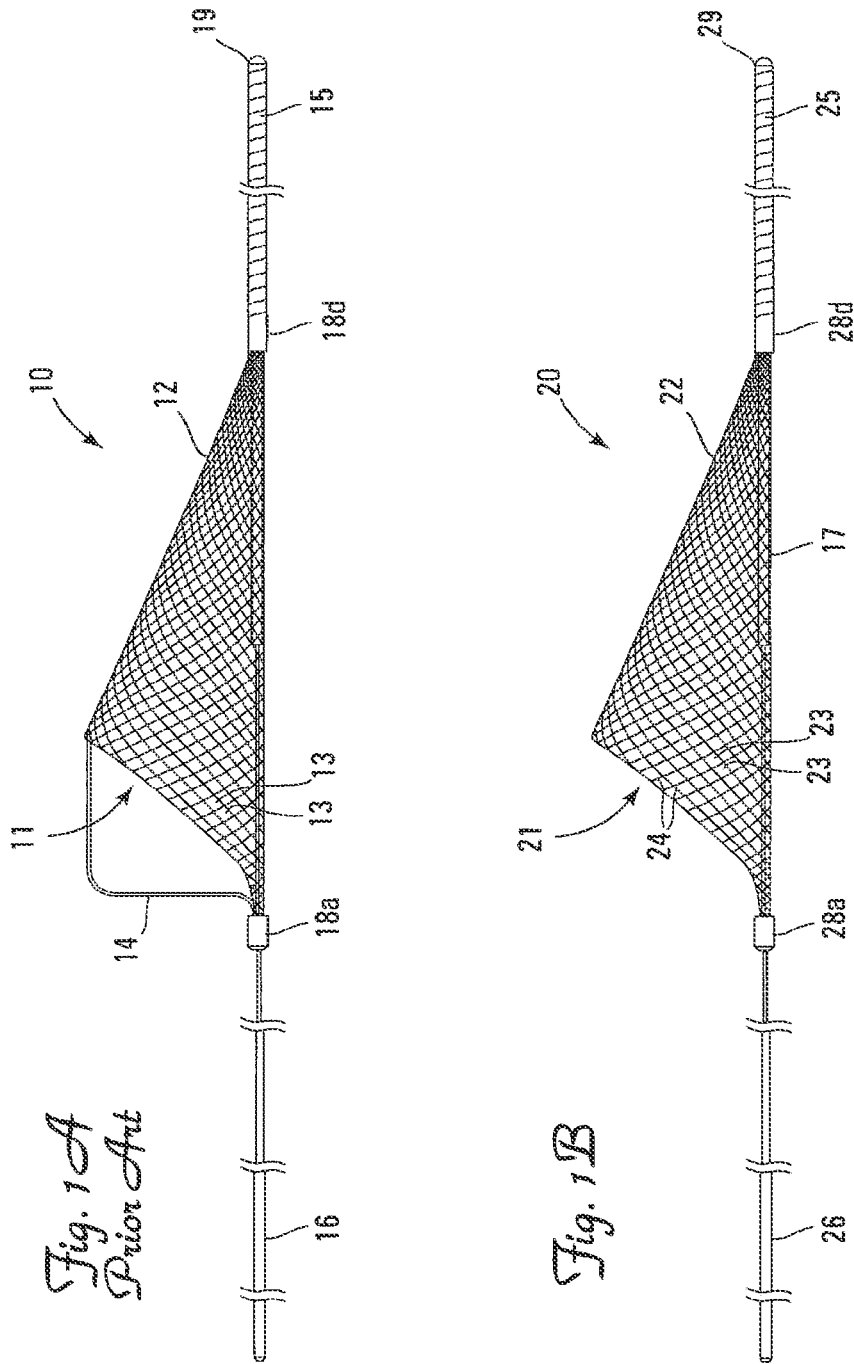

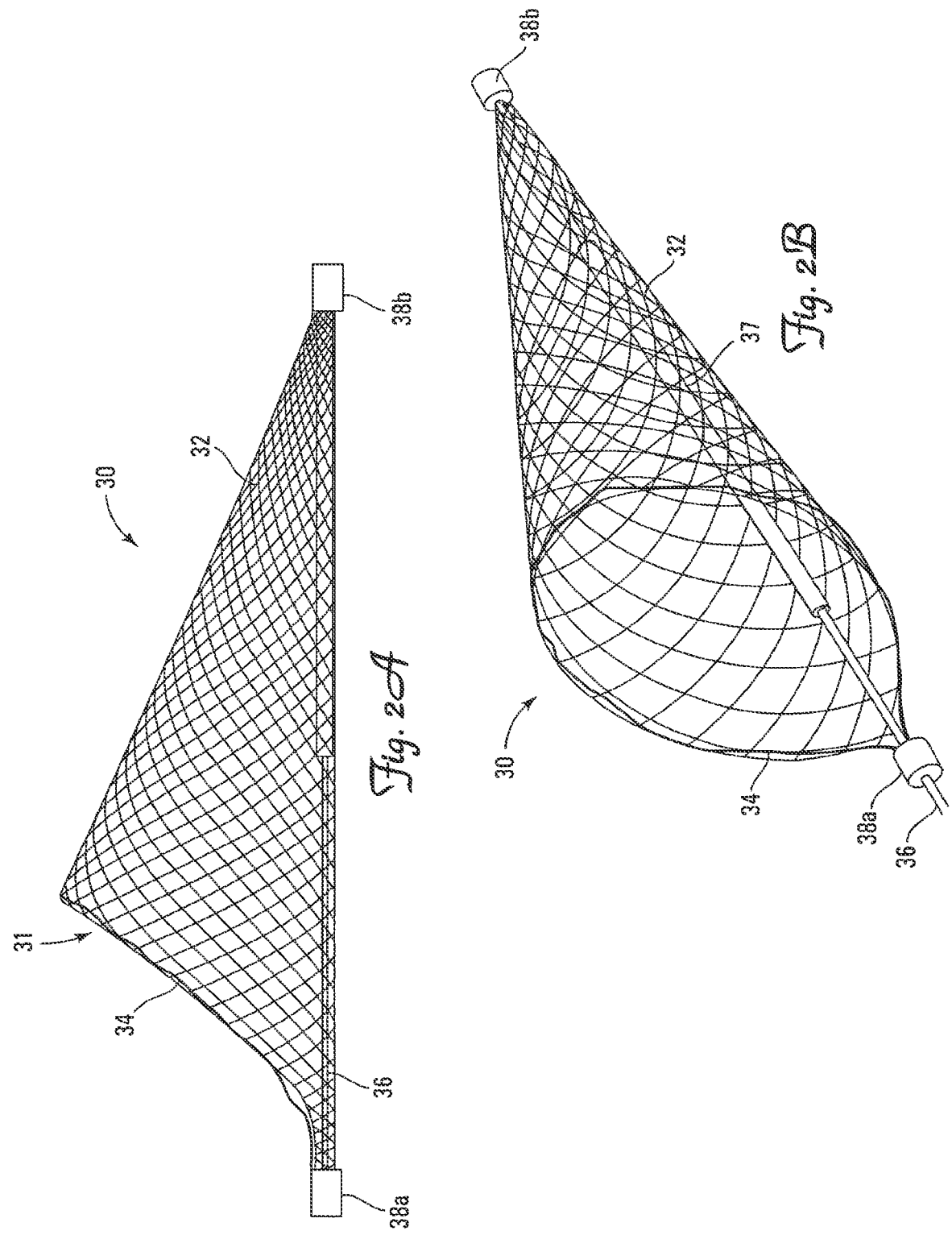

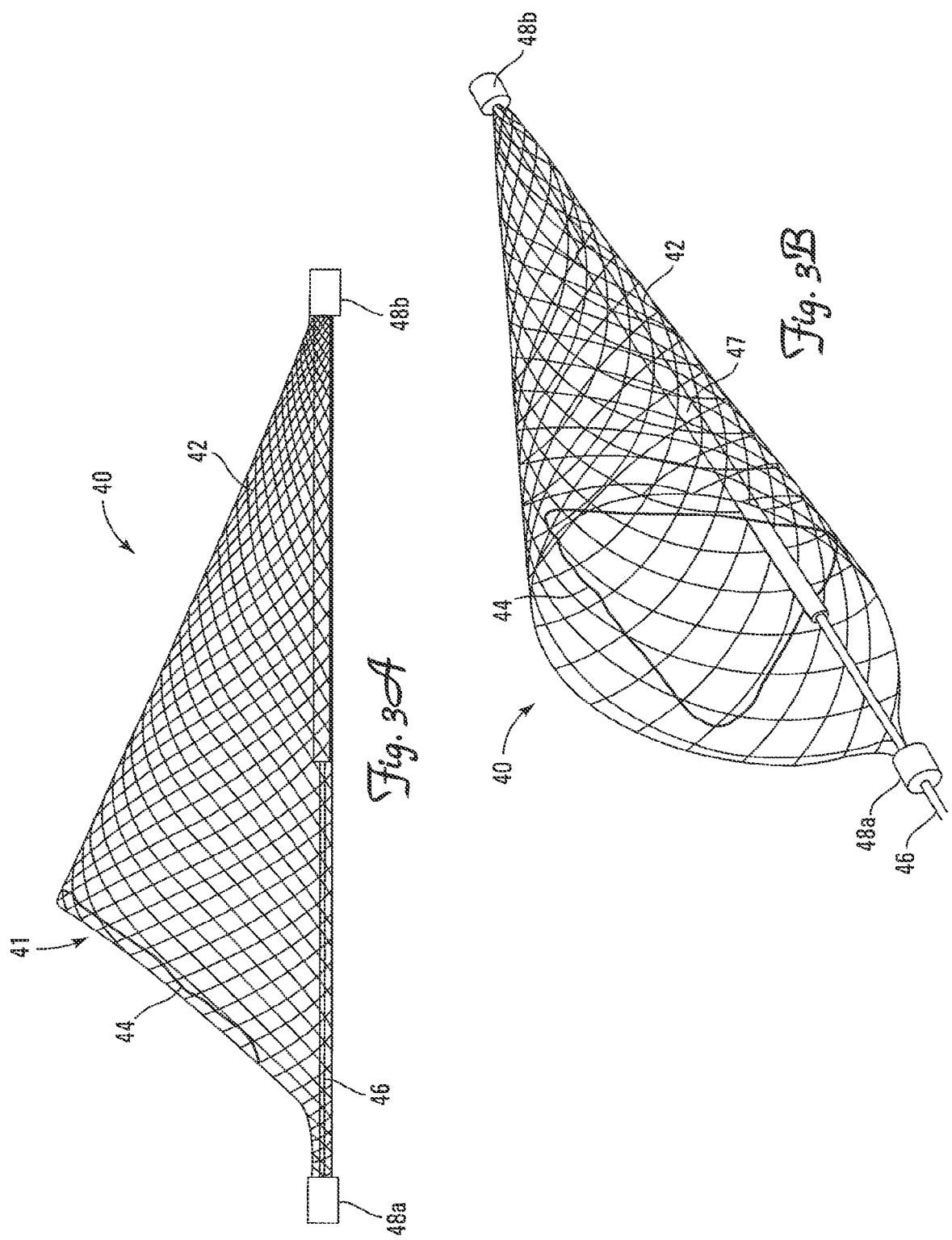

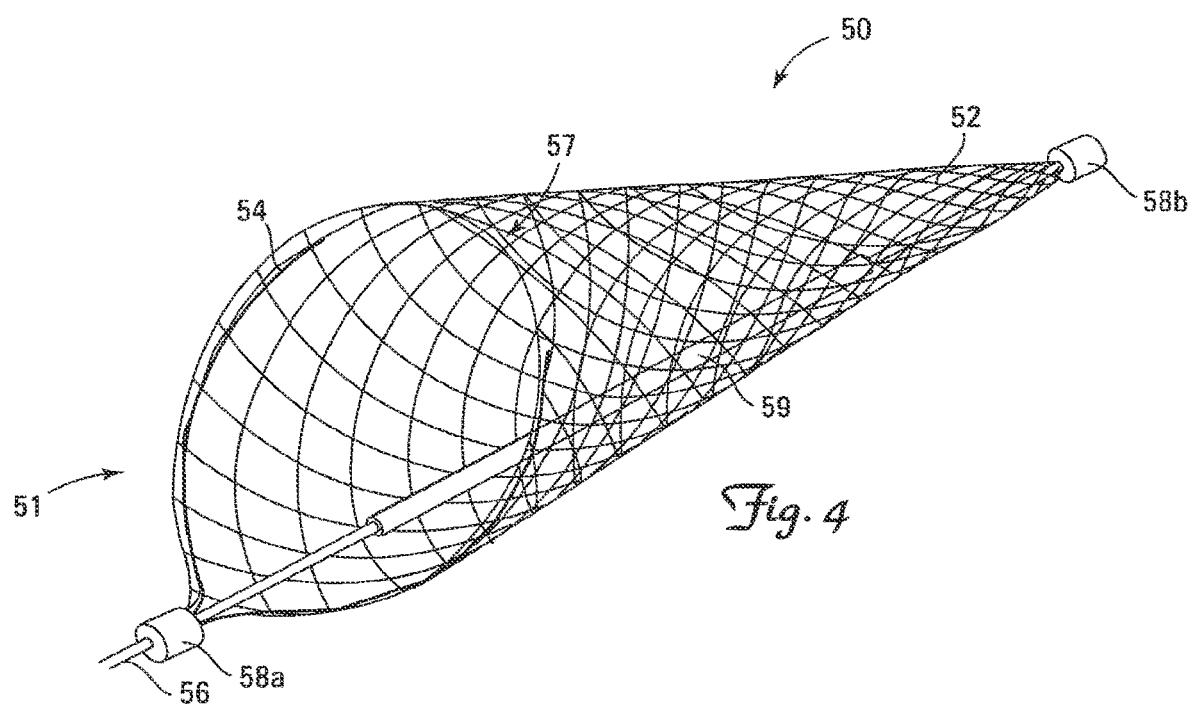

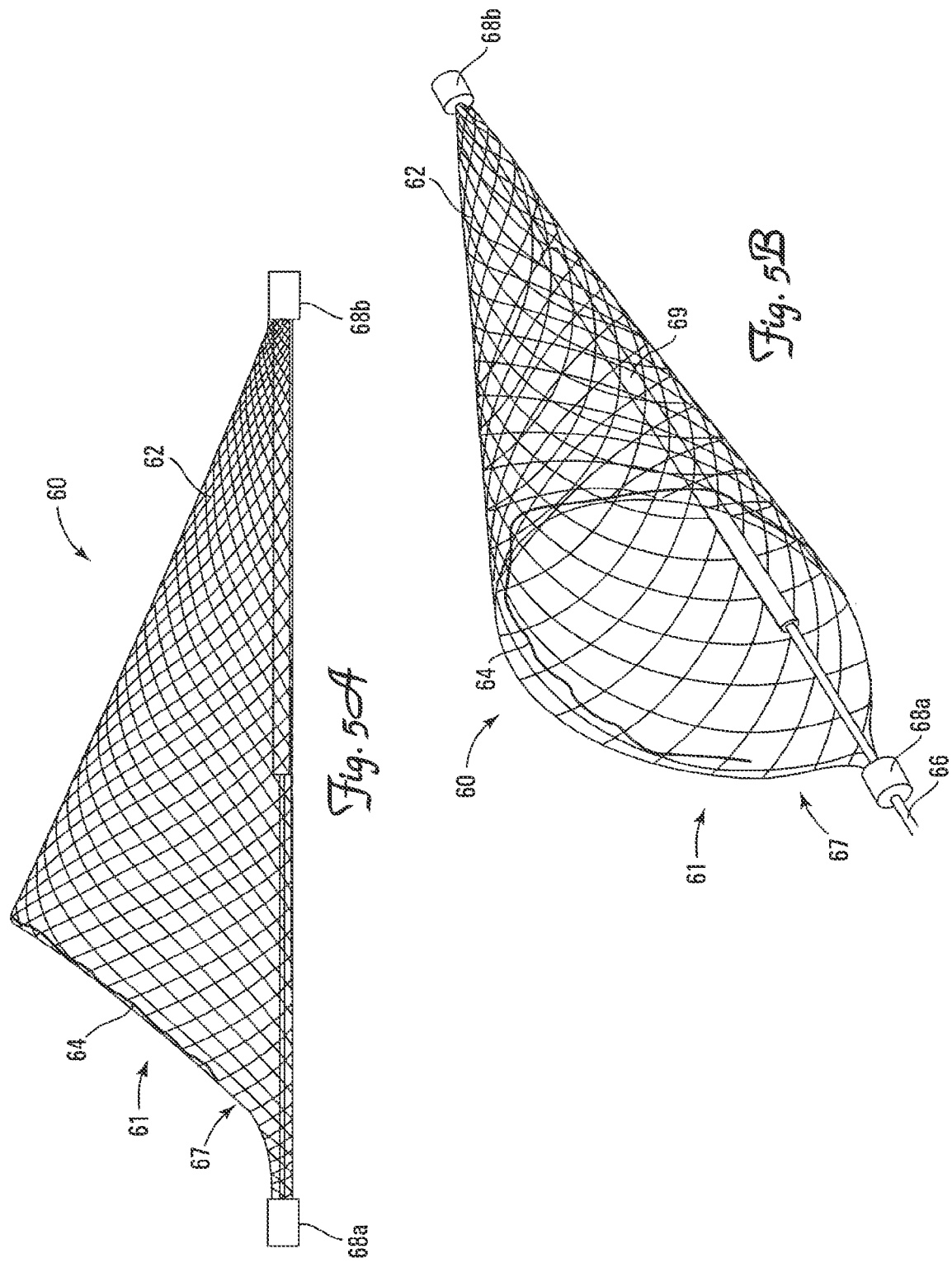

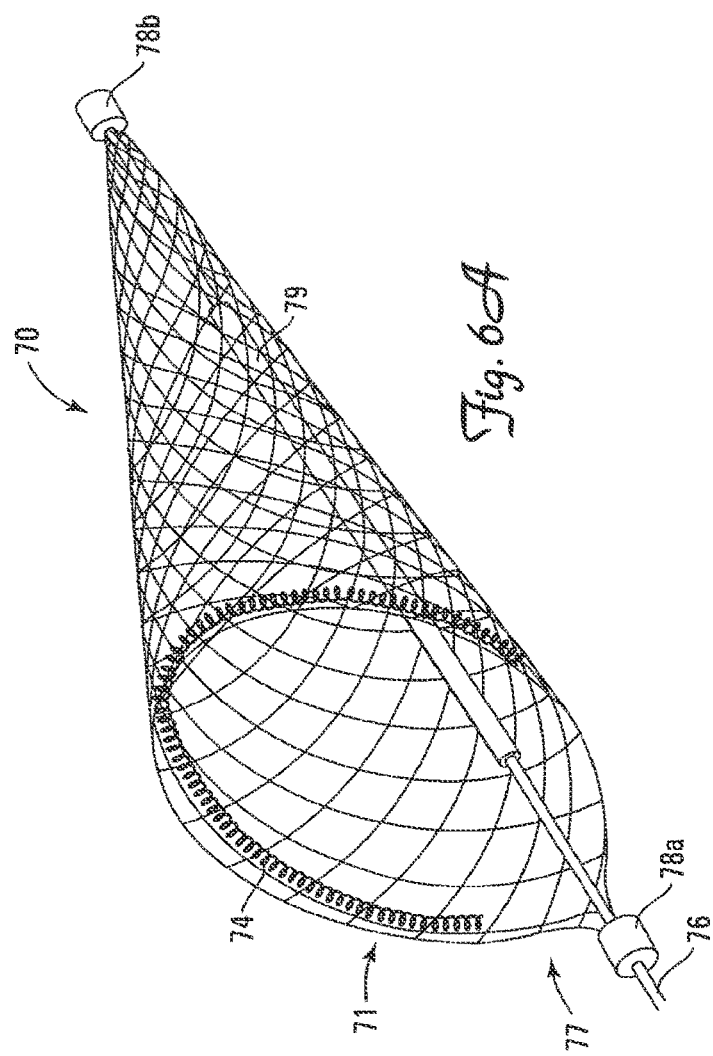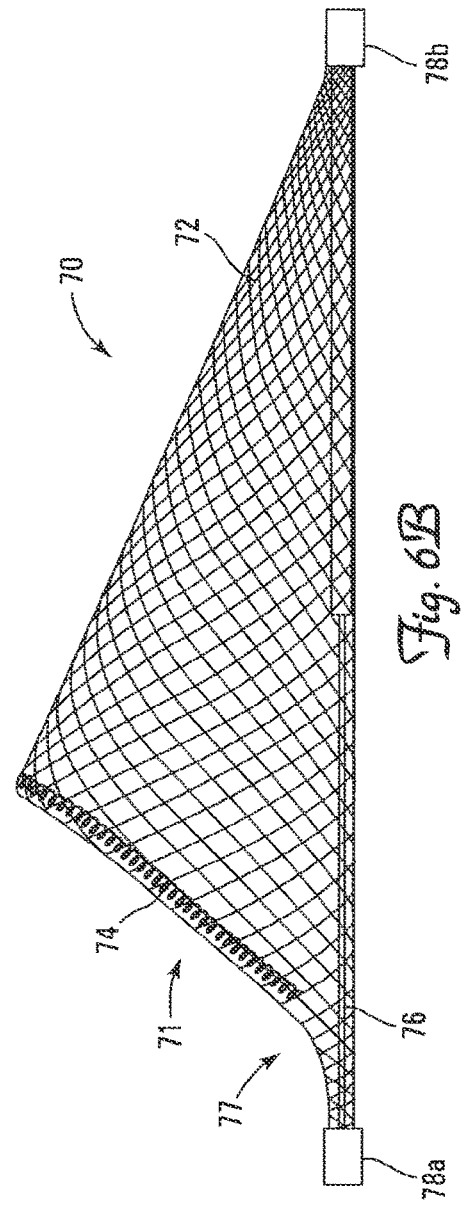

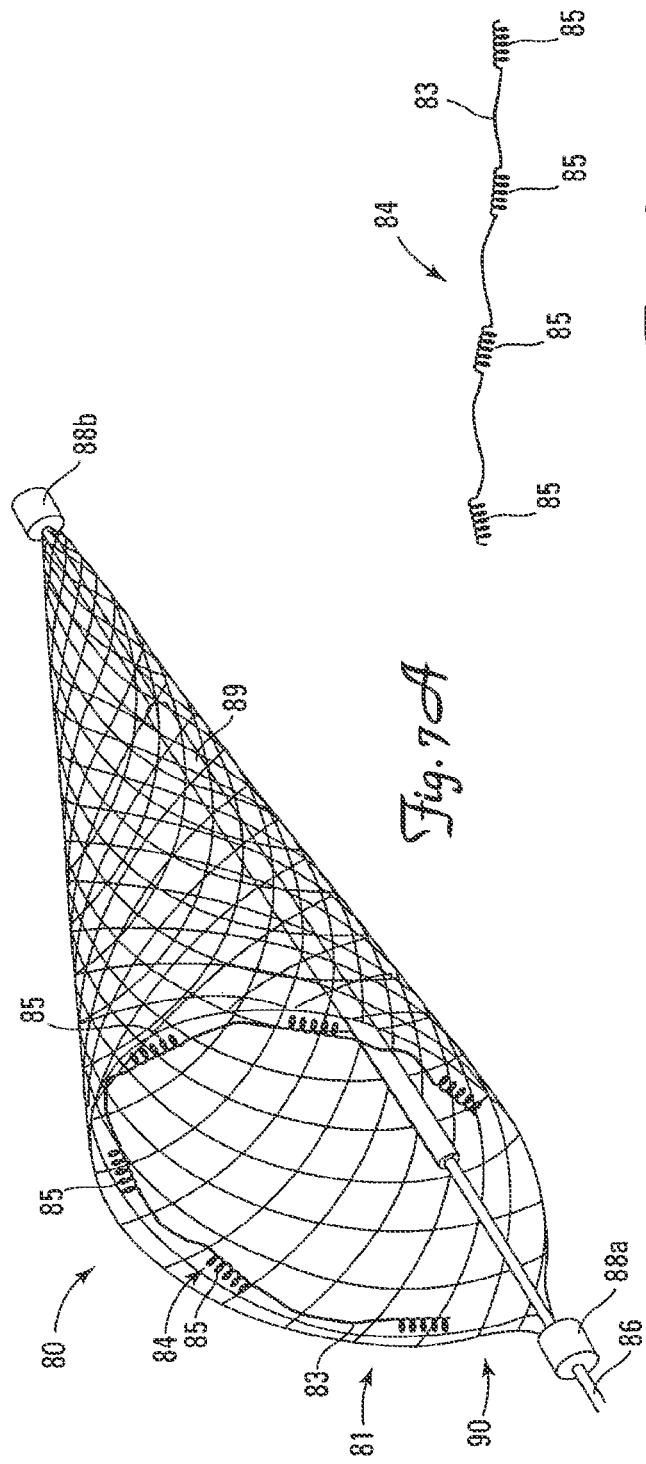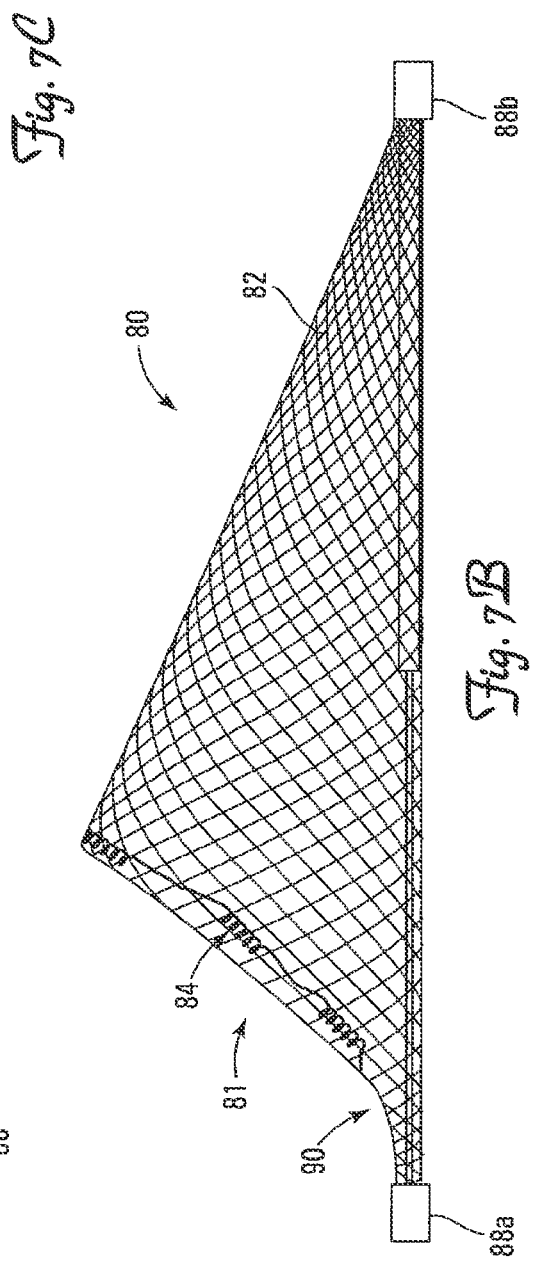

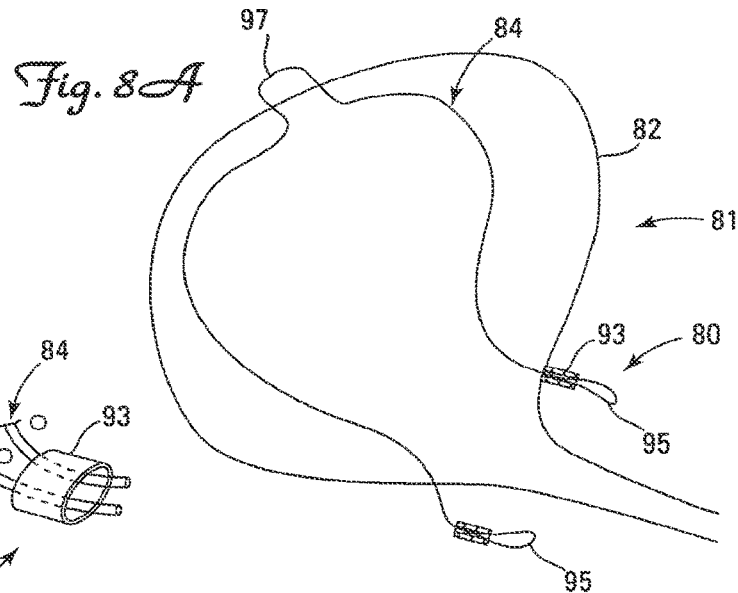
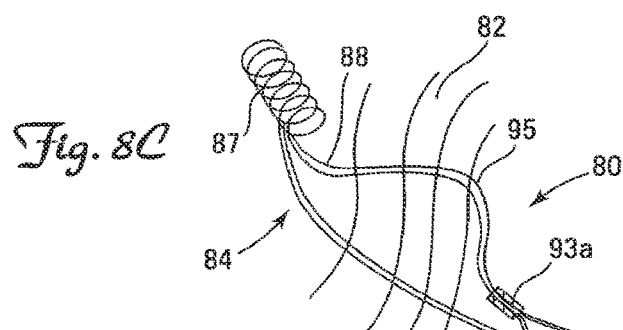
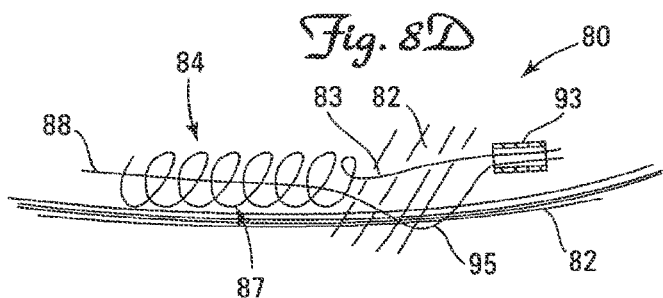
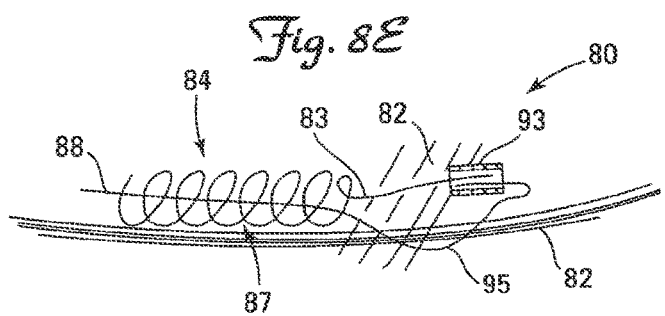

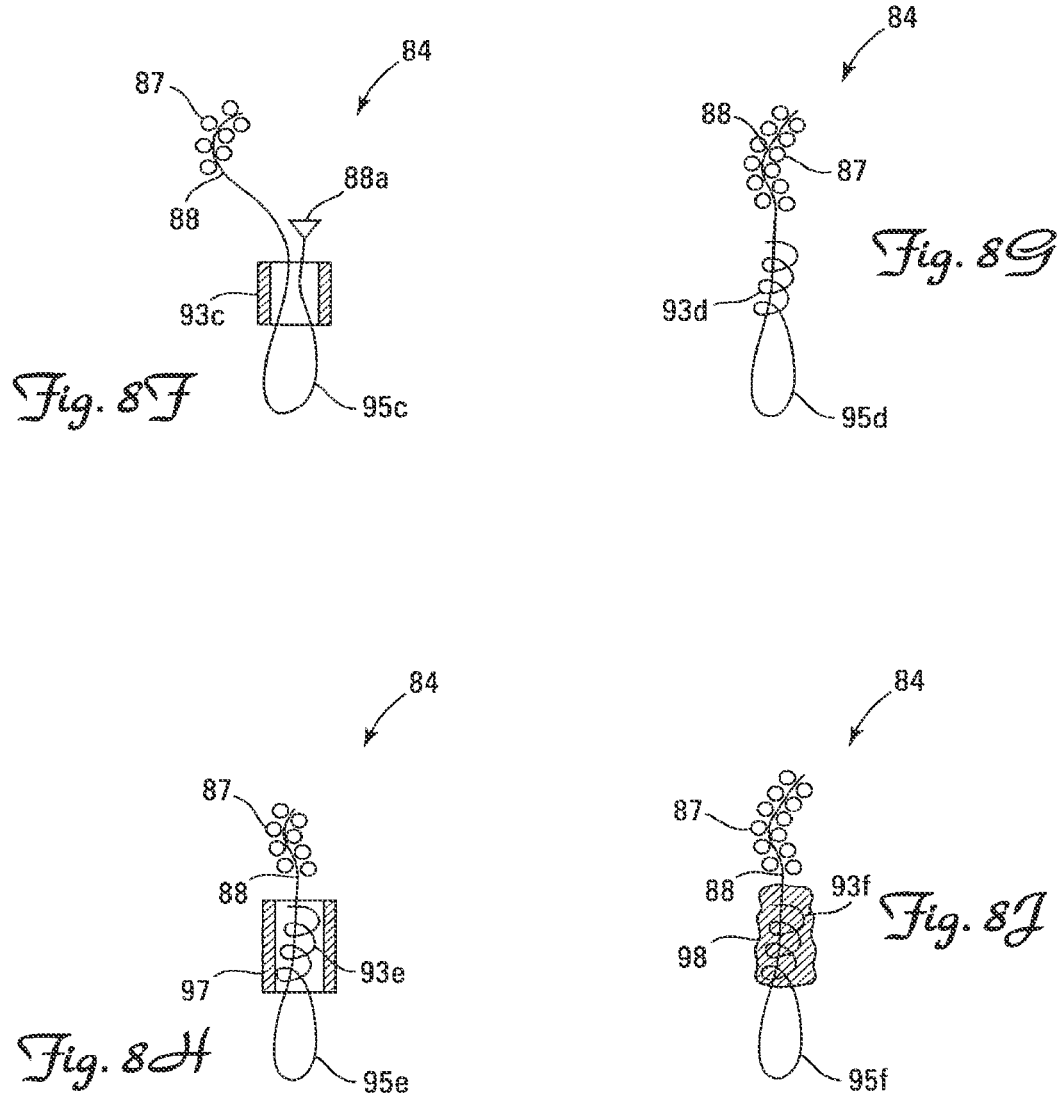

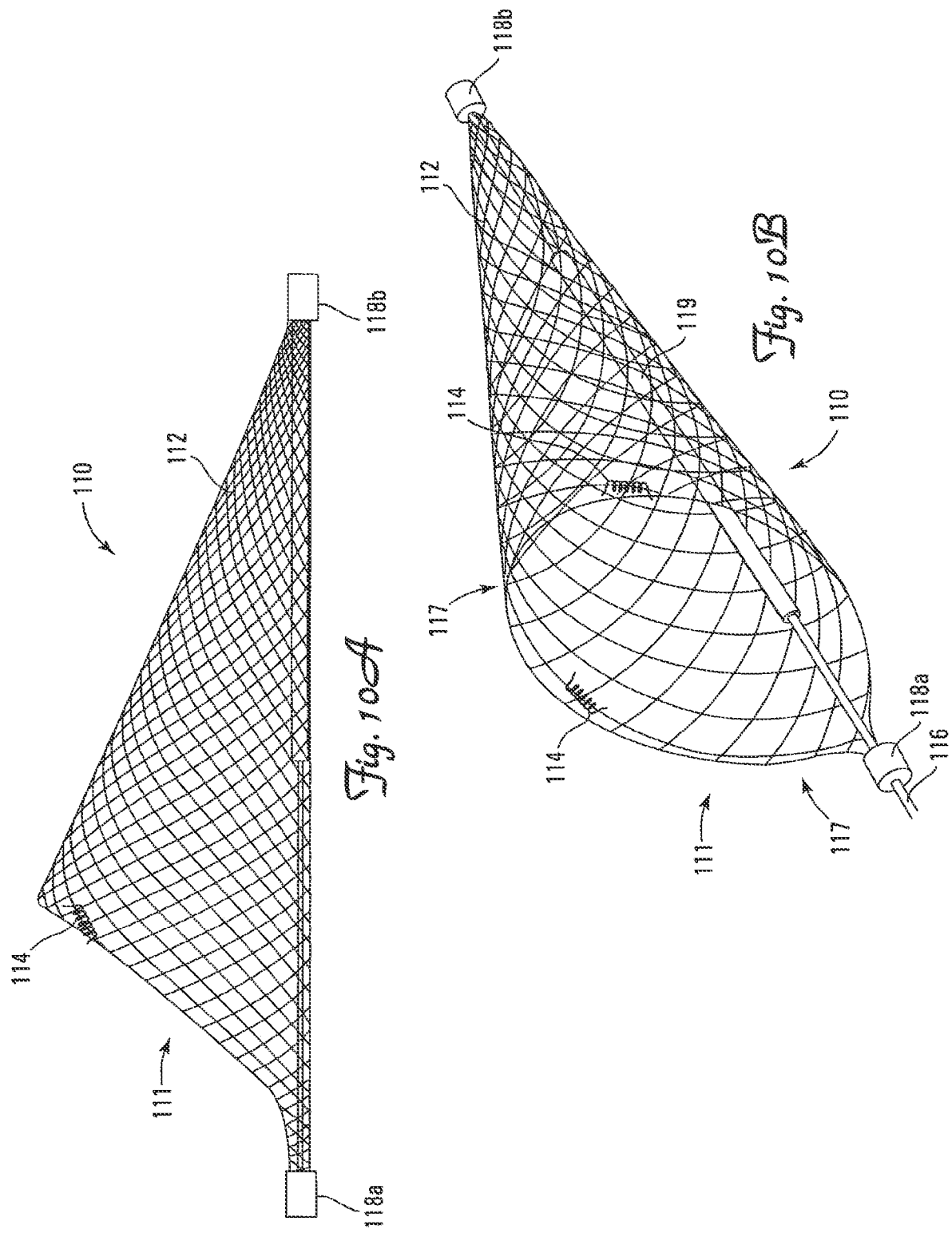

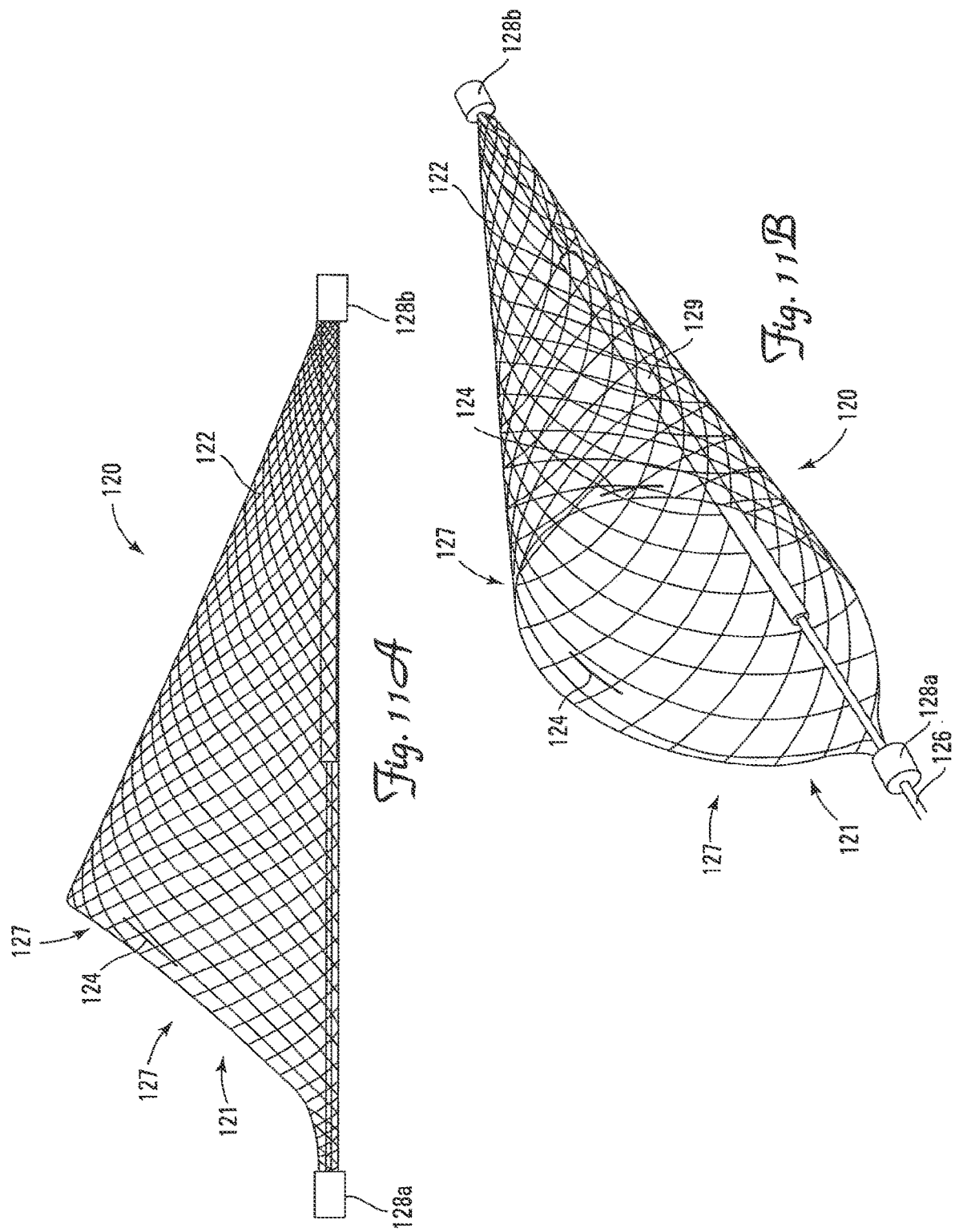

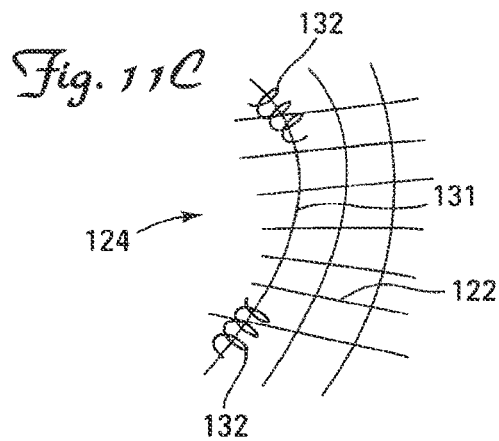
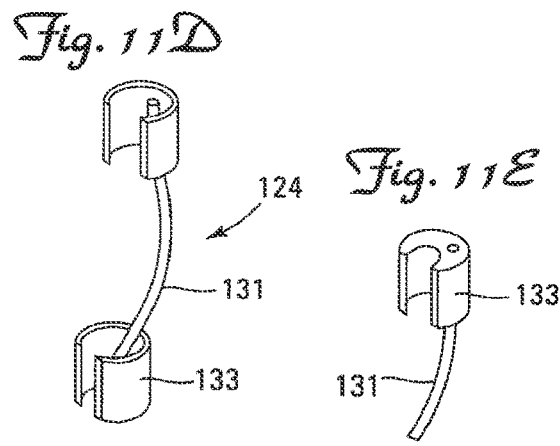
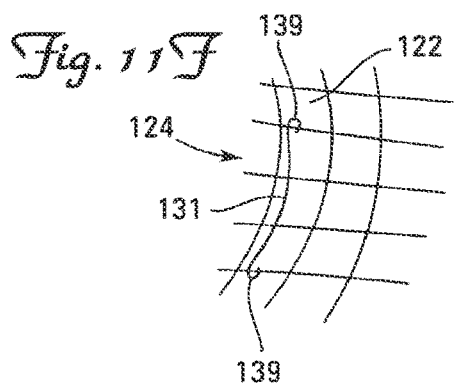
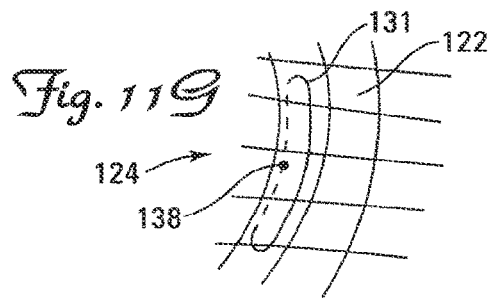
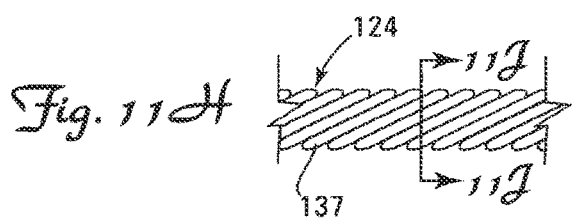
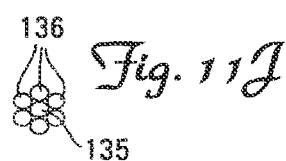
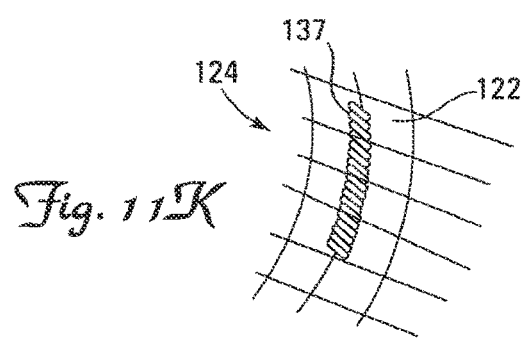

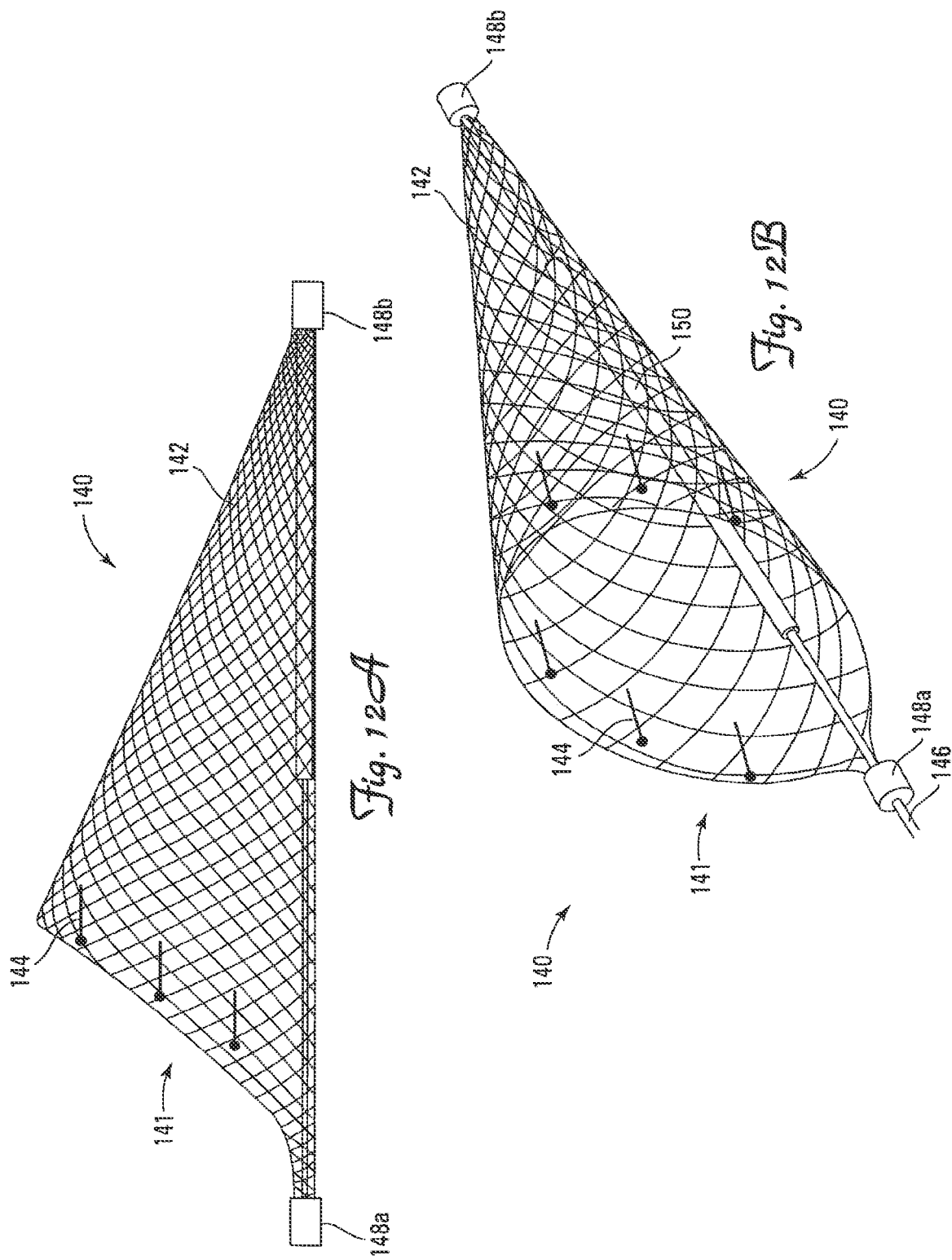

EMBOLIC PROTECTION DEVICES HAVING RADIOPAQUE ELEMENTS

This application is a continuation of U.S. patent application Ser. No. 11/729,324, filed Mar. 28, 2007, entitled, "EMBOLIC PROTECTION DEVICES HAVING RADIOPAQUE ELEMENTS," which claims the benefit of U.S. Provisional Application No. 60/788,255, filed Mar. 31, 2006, entitled "Embolic Protection Device having Radiopaque Markers," U.S. Provisional Application No. 60/800,147, filed May 12, 2006, entitled "Embolic Protection Device having Radiopaque Markers," and U.S. Provisional Application No. 60/831,751, filed Jul. 19, 2006, entitled "Embolic Protection Devices having Radiopaque Markers," the contents of each of which are hereby incorporated by reference herein.

FIELD OF THE INVENTION

The present invention relates to embolic protection systems, and, more particularly, to embolic protection systems for use in blood vessels.

BACKGROUND OF THE INVENTION

Vessels are commonly treated to reduce or eliminate narrowings caused by arteriosclerotic disease. Interventional treatments can include use of balloon angioplasty, stenting, thrombectomy, atherectomy, and other procedures. During treatment particulate debris can be generated at the treatment site. Infarcts, strokes, and other major or minor adverse events are caused when debris embolizes into vasculature from the treatment site.

To prevent embolization of debris, embolic protection devices have been developed. During a procedure such devices can be placed distal or proximal to the treatment site. Embolic protection devices can remove emboli from the bloodstream by filtering debris from blood, by occluding blood flow followed by aspiration of debris, or can cause blood flow reversal to effect removal of debris. The shape, length and other characteristics of an embolic protection device are typically chosen based on the anatomical characteristics in the vicinity of the treatment site. However, some anatomies present specific challenges due to the anatomical shape or configuration.

Difficulties can arise where embolic protection devices are not properly deployed within the anatomy. For example, if a device does not properly engage a lumenal wall, leaving a gap between the embolic protection device and the internal diameter of the lumen, then particulate matter entrained in a fluid in the lumen can bypass the protection device through the gap. It would be an advantage to be able to visualize whether or not there are any gaps between the embolic protection device and the lumenal wall. Also, when a protection device is being advanced or withdrawn from a lumen it may engage with an obstruction. The obstruction may be a stent that has been placed in a blood vessel, an area of plaque build-up, lumen tortuosity, or other structure. The operator of the embolic protection device may need to employ different techniques to advance or withdraw the device depending on the cause of engagement. Thus, it would be advantageous for the operator to be able to visualize the exact location of the device in the lumen.

Difficulties can also arise when recovering an embolic protection device. One problem that can occur is that the embolic protection device may require excessive force during recovery, for example when drawing the device into a recovery catheter. The causes of such excessive force can vary. For example, the device could be filled with embolic debris and thereby not fit into the lumen of a recovery catheter, the device may be caught on a structure such as a stent or a catheter tip, or other causes. It would be advantageous to the operator to visualize the embolic protection device so that appropriate actions can be taken so as to successfully recover the device. Further discussion of these issues is provided in U.S. Patent Publication No. 2002/0188314 A1, by Anderson et al., entitled "Radiopaque Distal Embolic Protection Device", the contents of which are incorporated herein by reference.

The current art employs a variety of approaches to solve the problem of visualizing an embolic protection device in a patient. All of the current approaches have limitations. For example, some devices have radiopaque coatings; however coatings may become separated from the underlying substrate. Radiopaque filler materials have been employed in polymer film devices; however the fillers detract from the mechanical properties of the films and the filler/film composites, being thin, are not very visible. Strands of drawn filled tubing (DFT) have been used and have good mechanical and radiopacity characteristics; however DFT is expensive. Individual strands of radiopaque wire, such as platinum, gold, tungsten, and their alloys have good radiopacity but can have unsuitable strength or elastic yield limits, and when these strands of radiopaque wire comprise a portion of the wires in a woven structure such as a braid, these strands can alter the braid wire spacing in the vicinity of the strand of radiopaque wire due to differing mechanical properties compared to neighboring non-radiopaque wires. For some filter devices, uniform wire spacing is desired and altered braid wire spacing can cause unacceptably large pores in the braid.

Accordingly, a need exists for an embolic protection device having improved radiopacity that is inexpensive, durable, provides visibility to the appropriate regions of the device, and which uses technology that does not compromise the performance of the device.

SUMMARY OF THE INVENTION

According to one aspect of the present invention, an embolic protection device comprises a mesh comprised of radiopaque and non-radiopaque elements. The mechanical properties and orientation of the radiopaque elements are selected to provide visibility under X-ray imaging of a region of an embolic protection device without compromising the ability to deploy and recover the device. The nonradiopaque elements can be superelastic. The radiopaque elements are woven into or affixed to the mesh at preferred locations within the device. A method is provided in which the device operator visualizes the radiopaque elements so as to guide how the device is utilized in a patient.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a discontinuous loop extending around a portion of a perimeter of the proximal facing opening, the discontinuous loop having a gap and the gap being proximate to the elongate support member.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of one or more beads.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of two or more discontinuous loop segments extending around a portion of a perimeter of the proximal facing opening.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of two or more discontinuous elongate segments extending around a portion of a perimeter of the proximal facing opening, the elongate segments being oriented in the same general direction as the elongate support member.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element comprising a wire having first and second coiled ends, the wire being twisted to form two loops, the filter element comprising a mesh and at least one loop of the radiopaque element encircling a portion of the mesh.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a discontinuous loop extending around a portion of the perimeter of the proximal facing opening, the discontinuous loop extending around a portion of the perimeter of the proximal facing opening, the filter element comprises a braided, self-expanding mesh, a portion of the elongate support member is disposed within the cavity, the filter element is attached to slidable proximal and distal markers that are disposed on the elongate support member, and the radiopaque element is attached to the proximal marker.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a loop extending around the perimeter of the proximal facing opening, the filter element comprises a braided, self-expanding mesh, a portion of the elongate support member is disposed within the cavity, the filter element is attached to slidable proximal and distal markers that are disposed on the elongate support member, the radiopaque element is attached to the device at two locations, the first location being the proximal marker and the second location being a region of the mesh that is diametrically opposed to the proximal mark.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a loop extending around a portion of a perimeter of the proximal facing opening, the loop not extending around the entire perimeter of the proximal facing opening.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the filter element is attached to slidable proximal and distal markers that are disposed on the elongate support member, the elongate support member comprises a connector that limits the movement of the slidable proximal and distal markers, and the connector comprises a flexibility enhancing structure.

The invention provides a method of deploying a device for filtering emboli from blood flowing through a lumen defined by the walls of a vessel in a patient's body comprising: providing the device for filtering emboli, the device comprising a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a discontinuous loop extending around a portion of a perimeter of the proximal facing opening, the discontinuous loop having a gap and the gap being proximate to the elongate support member; delivering the device percutaneously to a region of interest in the lumen of the patient's body; and using fluoroscopy to visualize the filter element in the lumen of the patient's body.

It is to be understood that that both the foregoing general description and the following detailed description are exemplary and explanatory and are intended to provide further explanation of the invention as claimed.

BRIEF DESCRIPTION OF THE DRAWINGS

The above and further advantages of the invention may be better understood by referring to the following description in conjunction with the accompanying drawings.

FIGS. 1A and 1B illustrate conceptually a side view of an embolic protection device having radiopaque and non-radiopaque elements.

FIGS. 2A and 2B illustrate conceptually side and isometric views of an embolic protection device having radiopaque elements in accordance with the present invention.

FIGS. 3A and 3B illustrate conceptually side or isometric views of an embolic protection device having radiopaque elements in accordance with the present invention.

FIG. 4 illustrates conceptually an isometric view of an embolic protection device having radiopaque elements in accordance with the present invention.

FIGS. 5A and 5B illustrate conceptually side or isometric views of an embolic protection device having radiopaque elements in accordance with the present invention.

FIGS. 6A and 6B illustrate conceptually side or isometric views of an embolic protection device having radiopaque elements in accordance with the present invention.

FIGS. 7A and 7B illustrate conceptually side or isometric views of an embolic protection device having radiopaque elements in accordance with the present invention.

FIG. 7C illustrates conceptually a plan view of a radiopaque element in accordance with the present invention.

FIGS. 8A to 8H, 8J, and 8K illustrate conceptually isometric or partial cross sectional views of radiopaque elements in accordance with the present invention.

FIGS. 10A and 10B illustrate conceptually side or isometric views of an embolic protection device having radiopaque markers in accordance with the present invention.

FIGS. 11A and 11B illustrate conceptually side or isometric views of an embolic protection device having radiopaque elements in accordance with the present invention.

FIGS. 11C to 11G illustrate conceptually side or isometric views of radiopaque elements in accordance with the present invention.

FIGS. 11H and 11J illustrate conceptually side or cross sectional views of a component of a radiopaque element in accordance with the present invention.

FIG. 11K illustrates conceptually a side view of a radiopaque element in accordance with the present invention.

FIGS. 12A and 12B illustrate conceptually side or isometric views of an embolic protection device having radiopaque elements in accordance with the present invention.

DETAILED DESCRIPTION OF THE INVENTION

Figure 1C:
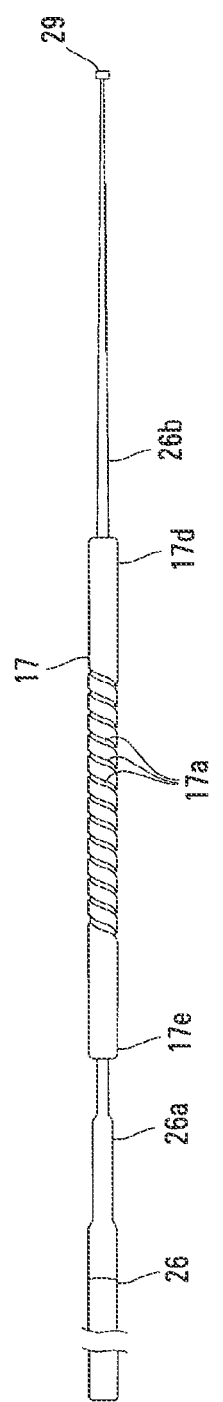
FIGS. 1C to 1F illustrate conceptually a side view of a component of an embolic protection device having radiopaque and non-radiopaque elements.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a discontinuous loop extending around a portion of a perimeter of the proximal facing opening, the discontinuous loop having a gap and the gap being proximate to the elongate support member. In one embodiment, the radiopaque element is made of metal or metal alloy. In another embodiment, the radiopaque element is made of gold, platinum, tungsten, tantalum, and alloys thereof.

In one embodiment, the filter element comprises a mesh; the radiopaque element may be interwoven through the mesh. In one embodiment, the mesh is braided. The filter element may be self-expanding or self-contracting. In one embodiment, a portion of the elongate support member is disposed within the cavity. In one embodiment, the radiopaque element is disposed around 50 to 90 percent of the perimeter of the proximal facing opening. In another embodiment, the radiopaque element is disposed around 70 to 80 percent of the perimeter of the proximal facing opening.

The radiopaque element may be a monofilament, a wire, a coiled wire, a wire comprising coiled segments and uncoiled segments, a multifilament wire, or a multifilament wire comprising a wire coiled around a core wire.

In one embodiment, the radiopaque element comprises a tang. In another embodiment, the radiopaque element comprises two loops, two bands, and one tang. In one embodiment, the filter element comprises a mesh and each loop encircles a portion of the mesh.

In one embodiment, the filter element comprises a mesh and the radiopaque element comprises a coiled portion, a loop, and a band, the loop encircling a portion of the mesh, and the loop and the band being covered by a protective mass.

In another embodiment, the filter element is attached to slidable proximal and distal markers that are disposed on the elongate support member.

In one embodiment, the radiopaque element comprises two bands and one tang. In another embodiment, the filter element comprises a mesh and each band encircles a portion of the mesh and a portion of the loop.

In one embodiment, the filter element comprises a mesh and the radiopaque element comprises a first loop encircling a portion of the mesh, a second loop and a first band disposed proximate the second loop, a third loop and a second band disposed proximate the third loop, the second loop and the first band being disposed within the third loop.

In another embodiment, the filter element comprises a mesh and the radiopaque element comprises a coiled portion, a central wire disposed within the coiled portion, a loop, and a band, the loop encircling a portion of the mesh.

In one embodiment, the radiopaque element comprises a protective mass. In another embodiment, the radiopaque element comprises an enlarged end that prevents it from passing through a band.

In one embodiment, the radiopaque element comprises a wire that has an end portion and the wire comprises a loop, an end portion of the wire being coiled back onto the wire to secure the loop. In another embodiment, the coiled portion of the wire is covered by a band. In another embodiment, the coiled portion of the wire is covered by a protective mass.

In one embodiment, the radiopaque element comprises a wire, a loop, a band, the wire having an enlarged diameter portion proximate the band. In another embodiment, the filter element comprises a mesh, the radiopaque element comprises a wire, a loop, and a band, the loop being attached to the mesh with a flexible strand.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of one or more beads. In one embodiment, the filter element comprises a mesh comprising strands and wherein the beads are tubular marker bands.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of two or more discontinuous loop segments extending around a portion of a perimeter of the proximal facing opening. The discontinuous loop segments may be wire, coiled wire, or stranded wire. In one embodiment, the filter element comprises a mesh and the discontinuous loop segments are loops of wire interwoven into the mesh.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of two or more discontinuous elongate segments extending around a portion of a perimeter of the proximal facing opening, the elongate segments being oriented in the same general direction as the elongate support member.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element comprising a wire having first and second coiled ends, the wire being twisted to form two loops, the filter element comprising a mesh and at least one loop of the radiopaque element encircling a portion of the mesh.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a discontinuous loop extending around a portion of the perimeter of the proximal facing opening, the discontinuous loop extending around a portion of the perimeter of the proximal facing opening, the filter element comprises a braided, self-expanding mesh, a portion of the elongate support member is disposed within the cavity, the filter element is attached to slidable proximal and distal markers that are disposed on the elongate support member, and the radiopaque element is attached to the proximal marker.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a loop extending around the perimeter of the proximal facing opening, the filter element comprises a braided, self-expanding mesh, a portion of the elongate support member is disposed within the cavity, the filter element is attached to slidable proximal and distal markers that are disposed on the elongate support member, the radiopaque element is attached to the device at two locations, the first location being the proximal marker and the second location being a region of the mesh that is diametrically opposed to the proximal marker.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a loop extending around a portion of a perimeter of the proximal facing opening, the loop not extending around the entire perimeter of the proximal facing opening.

The invention provides a device for filtering emboli from blood flowing through a lumen defined by the walls of a vessel in a patient's body, comprising: a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the filter element is attached to slidable proximal and distal markers that are disposed on the elongate support member, the elongate support member comprises a connector that limits the movement of the slidable proximal and distal markers, and the connector comprises a flexibility enhancing structure. In one embodiment, the flexibility enhancing structure is selected from slots, slits, holes, reduced thickness regions, or annealed regions.

The invention provides a method of deploying a device for filtering emboli from blood flowing through a lumen defined by the walls of a vessel in a patient's body comprising: providing the device for filtering emboli, the device comprising a filter element being expandable from a collapsed configuration when the filter element is restrained to an expanded configuration when the filter element is unrestrained, and an elongate support member, the filter being carried on a portion of the elongate support member, wherein the filter element has proximal and distal portions and a central portion, the filter element having a shape in the expanded configuration which defines a cavity having a proximal facing opening, and wherein the proximal portion of the filter element comprises a radiopaque element in the form of a discontinuous loop extending around a portion of a perimeter of the proximal facing opening, the discontinuous loop having a gap and the gap being proximate to the elongate support member; delivering the device percutaneously to a region of interest in the lumen of the patient's body; and using fluoroscopy to visualize the filter element in the lumen of the patient's body.

In the description below the invention is described using, as examples, filters comprised of braided metal strands. It is to be understood that the invention is not limited to the examples below. For example, the mesh of the invention can be comprised of strands that are woven, non-woven, or knitted to form the mesh. The mesh can have uniform strand spacing so as to define a structure with relatively uniformly sized openings between strands or can have variable strand spacing so as to define a structure with varied size openings between strands. The mesh can be coated with an elastic polymer film in whole or in part, or with another material, so as to reduce in size or eliminate the openings between strands. The coated or uncoated mesh may be partially or totally occlusive to flow of fluid or particles therethrough. In some embodiments, the metal strands may be superelastic alloys comprised of radiopaque alloy constituents. In some preferred embodiments, one or more metal strand is comprised of nickel-titanium-platinum or nickel-titanium-tantalum alloy. In addition, some or all of the strands may be comprised of materials other than metal including but not limited to engineering polymers such as polyetheretherketone (PEEK), liquid crystal, polyamide, or polyester; ceramics; glass-ceramics; metallic glasses; or other materials known in the art. In some embodiments, the aforementioned materials can be comprised of radiopaque filler materials. It is further understood that the cross section of some or all of the strands can be round, ovoid, square, rectangular, triangular, irregular, symmetrical, non-symmetrical, or other shapes.

In another aspect of the invention, the mesh can be comprised of a polymer film with holes produced by laser drilling, casting followed by dissolution of substances such as salts (leaving holes where the salt was dissolved), casting or forming into molds, or other methods as are known in the art. The mesh may be supported in whole or in part by struts comprised of metal, polymer, ceramic, metallic glass, or other materials. The struts may be aligned along the longitudinal axis of the embolic protective device, transverse to the longitudinal axis of the device, a combination of the two, or other orientations.

In the description below the invention is further described using as examples a generally conical shape embolic protective device with a proximal facing opening. It is to be understood that the invention is not limited to the examples below. For example, the embolic protective device of the invention can have a variety of other shapes such as generally cylindrical, cup-shaped, generally planar, or any other shape and may have a distally facing opening, proximal and distal openings, an opening off axis from the central longitudinal axis of the device, a sidewall opening, and no opening at all. The embolic protective device may be self-expanding, that is, have a tendency to radially or longitudinally expand, or both, when unconstrained; may be self-contracting, be partially both self-expanding and self-contracting; or may have no tendency to either expand or contract when not constrained. The embolic protective device may also be actively actuated radially or longitudinally or both by attaching a proximal end and a distal end of the device to telescoping structures, by using an inflatable structure such as a balloon to expand and contract the device, or by using other methods, as is known in the art.

Also in the description below the invention is described as comprised of radiopaque elements applied to an embolic protective device generally in the region of a proximal facing opening. It is to be understood that the invention is not limited to the examples below. For example, the radiopaque elements can be applied to an embolic protective device at other locations or regions of interest such as on the body of the device, at a midpoint of the device, at the distal end of the device, on ancillary structures other than the mesh of the device, and at other locations on the device.

It is understood that the radiopaque elements discussed below can be comprised of a range of radiopaque materials known in the art. Materials such as platinum, rhenium, iridium, tungsten, gold, lead, barium sulphate, bismuth oxychloride, bismuth subcarbonate, lead oxide, iodine containing compounds, barium containing compounds, ceramics, metallic glasses, and others may be used. Various physical forms comprised of radiopaque materials can be prepared and applied to embolic protective devices, such as monofilament wires, composite wires, stranded wires, cables, sheet, strip, mesh, sponge, sintered powders, powders or fibers embedded into matrices such as polymer matrices, tubes, and other forms.

Further, it is understood that elements compatible with Magnetic Resonance Imaging (MRI) or Ultrasonic (US) imaging can be applied to the embolic protective device in addition to or in the place of X-ray imageable elements in the examples below. For example, a marker of an embolic protective device may be comprised of non-ferrous wires such as tungsten and then imaged using MRI. The inventive device imaged by MRI can be MRI safe, that is, not move physically during application of the MRI associated electromagnetic fields, can be MRI compatible, that is not produce an imaging artifact on the image generated using MRI imaging, or a combination of both MRI safe and MRI compatible. Also by way of example, a marker of an embolic protective device may be comprised of a polymer material comprised of hollow glass microspheres and then imaged using US imaging. It is intended that references to radiopaque elements or markers in the examples given below apply as well to MRI elements or markers. It is further intended that references to radiopaque elements or markers in the examples given below apply as well to US elements or markers.

FIG. 1A illustrates an embolic protection device 10 having radiopaque and non-radiopaque elements. For clarity only the mesh along half of the perimeter of the device is shown. Embolic protection device 10 is comprised of mesh 12, proximal mouth marker 14, and host wire 16 having tip 19. Coil 15 is attached to tip 19 and is radiopaque. Proximal mouth marker 14 is radiopaque and is attached to proximal marker 18a. Mesh 12 is attached to proximal marker 18a and distal marker 18b and has opening 11. Proximal marker 18a and distal marker 18b slide relative to wire 16. Mesh 12 has an inner diameter, an outer diameter, and a thickness, is not radiopaque and has a number of pores 13 defined by the mesh. Each pore 13 has a size, the pore size defined as the area bounded by the mesh material forming the perimeter of the pore. Further description of a filter similar to that illustrated in FIG. 1A is disclosed in U.S. Pat. No. 6,325,815 B1 to Kusleika et al., entitled "Temporary Vascular Filter", the contents of which are incorporated herein by reference.

FIG. 1B illustrates another embolic protection device having radiopaque and non-radiopaque elements. For clarity only the mesh along half of the perimeter of the device is shown. Embolic protection device 20 is comprised of mesh 22, and host wire 26 having tip 29. Coil 25 is attached to tip 29 and is radiopaque. Mesh 22 has an inner diameter, an outer diameter, and a thickness, is attached to proximal marker 28a and distal marker 28b and has opening 21. Proximal marker 28a and distal marker 28b slide relative to wire 26. Mesh 22 is comprised of radiopaque filaments 24 and has a number of pores 23 defined by the mesh. Each pore 23 has a size, the pore size defined as the area bounded by the mesh material forming the perimeter of the pore. Further description of a filter similar to that illustrated in FIG. 1B is disclosed in U.S. Provisional Patent Application No. 60/775,818, filed Feb. 22, 2006, to Zaver et al., entitled "Embolic Protection System Having Radiopaque Filter Mesh", the contents of which are incorporated herein by reference.

As best illustrated in FIG. 1C, connector 17 joins proximal portion 26a of host wire 26 to distal portion 26b of host wire 26. Connector 17 can be made of metal, polymer, ceramic, or combinations of these materials. Suitable materials for connector 17 include stainless steels, shape memory materials, superelastic materials, PEEK, polyimide, polyester, ELGILOY®, PEBAX®, gold, platinum and its alloys, and other materials as are known in the art. Connector 17 may be comprised of flexibility enhancing structure 17a such as slots, slits, holes, reduced thickness regions, annealed regions, or other flexibility enhancing structures. Connector 17 is attached to host wire portions 26a, 26b by welding, crimping, soldering, adhesive bonding, brazing, press fit, or other methods known in the art. In one preferred embodiment, connector 17 is made of stainless steel tubing having a spiral slit cut through the wall thickness of the tubing over the central 65% of the length of the connector, joined to stainless steel host wire 26 proximal portion 26a over proximal region 17p by welding and joined to nitinol host wire 26 distal portion 26b over distal region 17d by crimping.

Figure 1D:
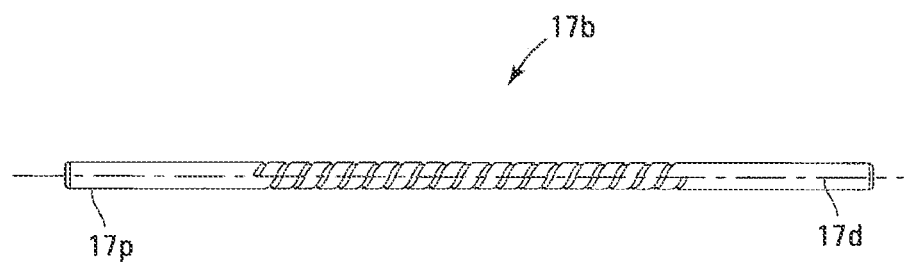
Figure 1E:
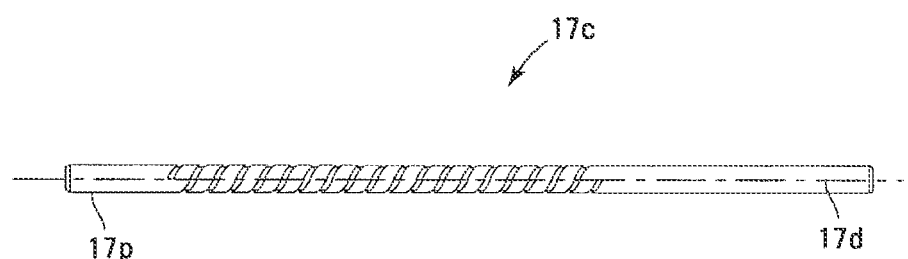
Figure 1F:
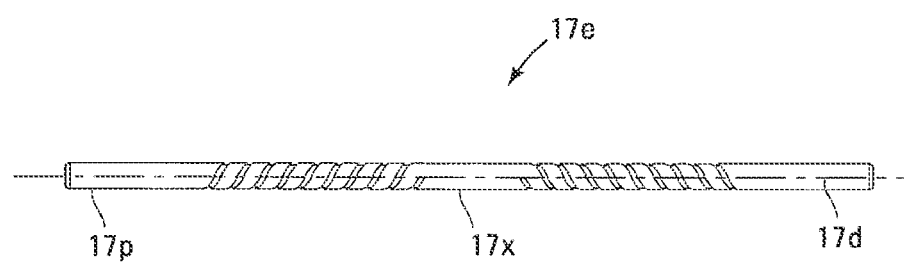

FIGS. 1D to 1F illustrate alternative embodiments of connector 17. FIGS. 1D and 1E have a single spiral cut through the wall thickness of tubular connector 17b and 17c respectively. In FIG. 1D the uncut region of connector 17b near proximal end 17p has the same length as the uncut region of connector 17b near distal end 17d. In FIG. 1E the uncut region of connector 17c near proximal end 17p has a shorter length than the uncut region of connector 17c near distal end 17d. In FIG. 1F the uncut regions of connector 17e near proximal end 17p and near distal end 17d have the same length, the connector has an uncut region 17x in between the two ends, and the cut regions have spiral cuts that spiral in opposite directions relative to each other. As will be understood to those of skill in the art, many different variations of flexible connectors are possible.

FIGS. 2A and 2B illustrate an embolic protection device having radiopaque elements in accordance with the present invention. For clarity only the mesh along half of the perimeter of the device is shown in FIG. 2A. Embolic protection device 30 is comprised of mesh 32 and host wire 36 having tip (not shown). Mesh 32 is attached to proximal marker 38a and distal marker 38b. Proximal marker 38a and distal marker 38b slide relative to wire 36. Connector 37 limits the movement of proximal marker 38a and distal marker 38b. Mesh 32 is comprised of radiopaque element 34 attached to proximal band 38a and comprises a continuous loop extending around perimeter of opening 31 of mesh 32. Radiopaque element 34 may extend around the inner diameter of mesh 32, external to diameter of mesh 32, or may be interwoven through thickness of mesh 32, and may or may not be fixedly attached to mesh 32. In a preferred embodiment, radiopaque filament 34 comprises stranded tungsten wire extending around the inner diameter of mesh 32 and interwoven through thickness of mesh 32 at one region diametrically opposite proximal marker 38a.

FIGS. 3A and 3B illustrate an embolic protection device having radiopaque elements in accordance with the present invention. For clarity only the mesh along half of the perimeter of the device is shown in FIGS. 3A and 3B. Embolic protection device 40 is comprised of mesh 42, and host wire 46 having tip (not shown). Mesh 42 is attached to proximal marker 48a and distal marker 48b. Proximal marker 48a and distal marker 48b slide relative to wire 46. Connector 47 limits the movement of proximal marker 48a and distal marker 48b. Mesh 42 is comprised of a continuous loop radiopaque element 44 threaded though thickness of mesh 42 and spanning opening 41 of mesh 42. Radiopaque filament 44 may be threaded through thickness of mesh at two, three, four, five, six, seven, eight, nine, ten, or any number of locations and may or may not be fixedly attached to mesh 42 at one or more locations. In a preferred embodiment, radiopaque filament 44 comprises gold plated tungsten wires coiled around a core of nitinol monofilament wire and threaded through thickness of mesh 42 at three locations equally spaced around perimeter of opening 44.

FIG. 4 illustrates an embolic protection device having radiopaque elements in accordance with the present invention. Embolic protection device 50 is comprised of mesh 52, radiopaque element 54, and host wire 56 having tip (not shown). Mesh 52 is attached to proximal marker 58a and distal marker 58b. Proximal marker 58a and distal marker 58b slide relative to wire 56. Connector 59 limits the movement of proximal marker 58a and distal marker 58b. Radiopaque element 54 is attached to proximal band 58a and comprises a discontinuous loop extending around perimeter of opening 51 of mesh 52 and having gap 57. Radiopaque element 54 may extend around the inner diameter of mesh 52, external to diameter of mesh 52, or may be interwoven through thickness of mesh 52, and may or may not be fixedly attached to mesh 52. Radiopaque element 54 may extend around 10%, 20%, 30%, 40%, 50%, 60%, 70%, 80%, 90%, or any other percentage of perimeter of opening 51. In a preferred embodiment, radiopaque element 54 comprises gold plated tungsten wires coiled around a core of nitinol monofilament wire extending around 75% of perimeter of opening 51 along inner diameter of mesh 52 and not interwoven through thickness of mesh 52.

FIGS. 5A and 5B illustrate an embolic protection device having radiopaque elements in accordance with the present invention. Embolic protection device 60 is comprised of mesh 62, radiopaque element 64, and host wire 66 having tip (not shown). Mesh 62 is attached to proximal marker 68a and distal marker 68b. Proximal marker 68a and distal marker 68b slide relative to wire 66. Connector 69 limits the movement of proximal marker 68a and distal marker 68b. Radiopaque element 64 comprises a discontinuous loop extending around perimeter of opening 61 of mesh 62 and having gap 67. Radiopaque element 64 may extend around the inner diameter of mesh 62, external to diameter of mesh 62, or may be interwoven through thickness of mesh 62, and may or may not be fixedly attached to mesh 62. Radiopaque element 64 may be attached to mesh by inserting both a portion of radiopaque element 64 and a portion of mesh 62 into a lengthwise slotted cylindrical metallic marker band (not shown) and then crimping the band to attach mesh 62 to element 64. Radiopaque element 64 may extend around 10%, 20%, 30%, 40%, 50%, 60%, 70%, 80%, 90%, or any other percentage of perimeter of opening 61. In a preferred embodiment, radiopaque element 64 comprises gold plated tungsten wires coiled around a core of nitinol monofilament wire extending around 75% of perimeter of opening 61 along inner diameter of mesh 62 and interwoven through thickness of mesh 62 at one region diametrically opposite proximal marker 68a.

FIGS. 6A and 6B illustrate an embolic protection device having radiopaque elements in accordance with the present invention. Embolic protection device 70 is comprised of mesh 72, radiopaque element 74, and host wire 76 having tip (not shown). Mesh 72 is attached to proximal marker 78a and distal marker 78b. Proximal marker 78a and distal marker 78b slide relative to wire 76. Connector 79 limits the movement of proximal marker 78a and distal marker 78b. Radiopaque element 74 comprises a discontinuous loop extending around perimeter of opening 71 of mesh 72 and having gap 77. Radiopaque element 74 is comprised of a coil configuration and is interwoven through thickness of mesh 72, and may or may not be fixedly attached to mesh 72 by means of a slotted marker band, adhesive, welding, soldering, or other means. Radiopaque element 74 may extend around 10%, 20%, 30%, 40%, 50%, 60%, 70%, 80%, 90%, or any other percentage of perimeter of opening 71. In a preferred embodiment, radiopaque element 74 comprises gold plated tungsten wires coiled around thickness of mesh 72 at perimeter of opening 71 and extending around 75% of perimeter of opening 71.

FIGS. 7A to 7C illustrate an embolic protection device having radiopaque elements in accordance with the present invention. Embolic protection device 80 is comprised of mesh 82, radiopaque element 84, and host wire 86 having tip (not shown). Mesh 82 is attached to proximal marker 88a and distal marker 88b. Proximal marker 88a and distal marker 88b slide relative to wire 86. Connector 89 limits the movement of proximal marker 88a and distal marker 88b. Radiopaque element 84 comprises a discontinuous loop extending around perimeter of opening 81 of mesh 82 having gap 90, coiled segments 85, and uncoiled segments 83. Radiopaque element 84 may extend around the inner diameter of mesh 82, external to diameter of mesh 82, or may be interwoven through thickness of mesh 82, and may or may not be fixedly attached to mesh 82 by means of a slotted marker band, adhesive, welding, soldering, or other means. Radiopaque element 84 may extend around 10%, 20%, 30%, 40%, 50%, 60%, 70%, 80%, 90%, or any other percentage of perimeter of opening 81. In a preferred embodiment, radiopaque element 84 comprises six coiled segments 85, and five uncoiled segments 83 of gold plated tungsten wire coiled extending around 60% of inner diameter of mesh 82 near perimeter of opening 81 and interwoven through mesh 82 at a region diametrically opposite to proximal marker 88*a* and at regions near both ends of radiopaque element 84. Coiled segments 85 and uncoiled segments 83 may be made from a single piece of wire that has been coiled in certain regions, may be made from discrete coiled and uncoiled segments that have been connected by welding, mechanical interlock, bonded, soldered, brazed, or other means, may be made by attaching discrete coiled segments onto a continuous length of wire, or other methods known in the art.

FIGS. 8A to 8E illustrate alternative embodiments of radiopaque elements in accordance with the present invention. Radiopaque element 84 is comprised of central wire 88, coiled radiopaque wire 87, one or more bands 93 and optionally may be comprised of one or more loops 95 and optionally may be comprised of one or more tangs 97. Central wire 88 may be comprised of metal or engineering polymer such as stainless steel, nitinol, polyimide, PEEK, nylon, polyester or other materials, and may be comprised of monofilament, stranded, or cable construction. Coiled radiopaque wire 87 may be comprised of radiopaque material such as gold, tungsten, platinum, platinum alloy or other materials. Band 93 may be metal or polymer such as gold, tungsten, platinum, platinum alloy, stainless steel, polyimide, PEEK, nylon, or other materials, may be a solid walled tube, a longitudinally split tube, or a tube comprised of a wound coil, and may shrink in diameter on application of heat. Radiopaque element 84 may be pre-fabricated prior to attachment to mesh 82. Band 93 attaches radiopaque element to itself using methods such as crimping, by comprising a reservoir for adhesive bonding, by reflowing solder into the band, by heat fusing, or other methods known in the art. Loop 95 retains radiopaque element 84 in connection to mesh 82 and optionally may encircle a portion of the mesh such as through the thickness of mesh. Tang 97 provides a strain relief function to radiopaque element 84 during compression of element 84 into a smaller size, for example during retraction of embolic protection device 80 into a delivery catheter.

In FIG. 8A radiopaque element 84 is positioned near opening 81 of mesh 82 and has two loops 95, two bands 93, and one tang 97. In a preferred embodiment, each loop 95 encircles mesh 82 through the thickness of mesh 82 and each band 93 is crimped to attach the radiopaque element to itself. In an alternative embodiment, FIG. 8B illustrates band 93 attaching radiopaque element 84 to itself and around a portion of mesh 82.

FIG. 8C illustrates radiopaque element 84 having three loops 95, 95*a*, and 95*b*, two bands 93*a* and 93*b*, straight segment 83, and central wire 88. Loop 95 encircles through the thickness of a portion of mesh 82, and bands 93*a* and 93*b* attach radiopaque element 84 to itself. Loops 95*a* and 95*b* do not encircle mesh 82. Loop 95*b*, formed from straight segment 83, and band 93*b* are pulled through loop 95*a*, formed from wire 88, to interlock the radiopaque element to itself and around the thickness of mesh 82. In a preferred embodiment, loop 95*a* is biased to self-contract to an opening size at rest smaller than the opening size required to pass loop 95*b* and band 93*b* therethrough.

FIGS. 8D and 8E illustrate radiopaque element 84 having loop 95, bands 93, central wire 88 and straight segment 83. Loop 95 encircles through the thickness of a portion of mesh 82, and band 93 attaches straight segment 83 to wire 88. In FIG. 8D the free ends of straight segment 83 and wire 88 are inserted into one end of band 93. In FIG. 8E the free ends of straight segment 83 and wire 88 are inserted into opposite ends of band 93.

FIG. 8F illustrates radiopaque element 84 having loop 95*c*, band 93*c*, central wire 88, coiled radiopaque wire 87 and enlarged central wire end 88*a*. Central wire end is enlarged by mechanical deformation techniques such as cold forming, hot forming, forming a molten droplet and allowing to cool, by addition of soldered, bonded or crimped material, or other methods. Band 93*c* attaches central wire 88 to itself and enlarged end 88*a* prevents the end of central wire 88 from passing through attached band 93*c*.

FIG. 8G illustrates radiopaque element 84 having loop 95*d*, band 93*d*, central wire 88 and coiled radiopaque wire 87. Band 93*d* is comprised of a coiled end portion of central wire 88. In a preferred embodiment, central wire 88 is made of nitinol and band 93*d* is made by coiling and heat setting the end portion of central wire 88. Band 93*d* attaches central wire 88 to itself by passing central wire through band 93*d*.

FIG. 8H illustrates radiopaque element 84 with some similarities to radiopaque element 84 illustrated in FIG. 8G having loop 95*e*, band 93*e*, central wire 88 and coiled radiopaque wire 87. Band 93*e* is comprised of a coiled end portion of central wire 88 and the coiled portion is surrounded by tubing 97. Tubing 97 may be comprised of heat shrink polymer tubing, metal tubing with or without solder wicked inside, polymer tubing with or without adhesive inside or other materials. Band 93*e* attaches central wire 88 to itself by passing central wire through band 93*e*.

FIG. 8J illustrates radiopaque element 84 with some similarities to radiopaque element 84 illustrated in FIG. 8G having loop 95*f*, band 93*f*, central wire 88 and coiled radiopaque wire 87. Band 93*f* is comprised of a coiled end portion of central wire 88 and the coiled portion is surrounded by mass 98. Mass 98 may be comprised of adhesive, UV-curable adhesive, metallic solder or other materials. Band 93*f* attaches central wire 88 to itself by passing central wire through band 93*f*.

Figure 8K:
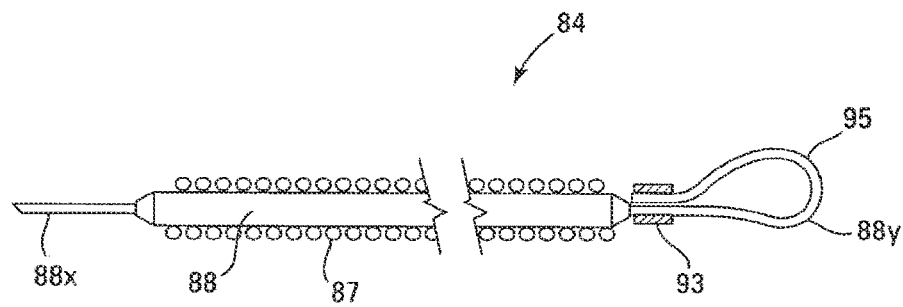

FIG. 8K illustrates radiopaque element 84 having loop 95, band 93, central wire 88 and coiled radiopaque wire 87. Central wire 88 is comprised of reduced diameter end portions 88*x*, 88*y*. Band 93 attaches central wire 88 to itself by passing central wire through band 93 (shown assembled for end 88*y*). Band 93 is prevented from migrating towards central portion of core wire 88 due to the enlarged diameter of the central portion as compared to that of the reduced diameter end portions 88*x*, 88*y*.

Figure 8L:
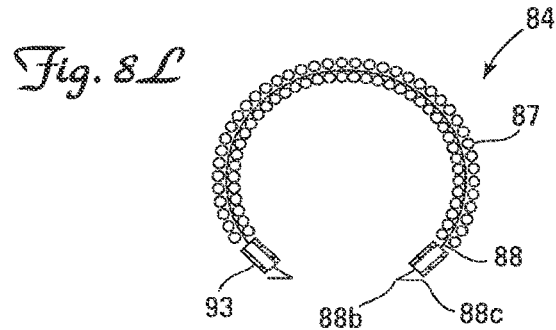
FIGS. 8L to 8N illustrate conceptually a method for assembling a radiopaque element to an embolic protection device in accordance with the present invention.
Figure 8M:
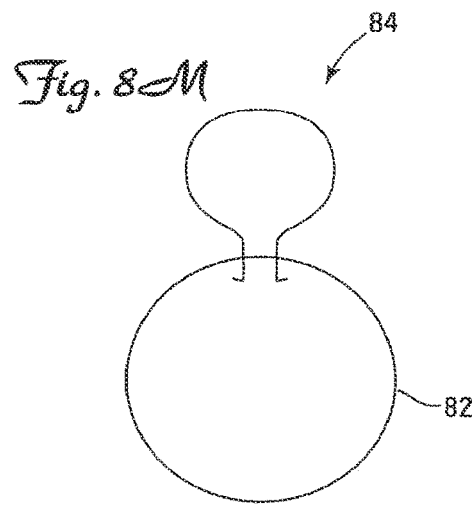
Figure 8N:
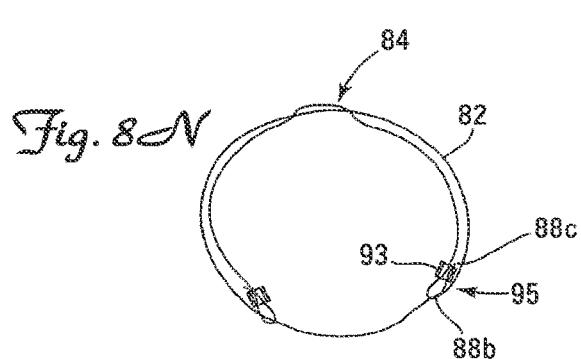

An exemplary method of manufacturing an embolic protective device having radiopaque elements 84 in accordance with the present invention is now described in connection with FIGS. 8L to 8N. Central wire 88 made of nitinol is bent into a circular shape having bend regions 88*b* on a fixture (not shown) and heat set to remember the shape using techniques well known in the art. Coiled radiopaque wire 87 and two bands 93 are slid onto central wire 88 (FIG. 8L). Bend regions 88*b* are passed through mesh 82 near the 12:00 position of an embolic protection device (shown schematically in FIG. 8M) and again through mesh 82 near the 5:00 and 7:00 positions. Central wire ends 88*c* are passed through bands 93 and bands 93 are attached to central wire 88 (FIG. 8N), forming loops 95.

Figure 8P:
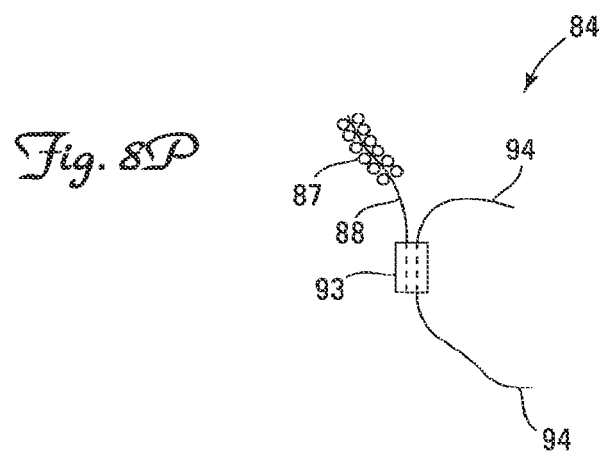
FIGS. 8P to 8R illustrate conceptually side views of radiopaque elements in accordance with the present invention.

In another embodiment, radiopaque elements 84 incorporating flexible strands and in accordance with the present invention are described in connection with FIGS. 8P and 8Q. FIG. 8P illustrates radiopaque element 84 having band 93, central wire 88, coiled radiopaque wire 87 and flexible strand 94. Band 93 attaches central wire 88 to flexible strand 94 by crimping, swaging, shrink fit, or other means and optionally band 93 may be filled with adhesive, solder, or other attachment substance. Flexible strand 94 may be comprised of KEVLAR®, carbon fiber, polyester, nitinol, suture, or other materials in monofilament, stranded, or cable constructions. Suture, if used, may be monofilament, braided, or stranded, may be made of polypropylene, polyester, silk, gut, metal, or other materials, may have diameters ranging from 3/0 to 10/0 (0.2 mm to 0.02 mm), and may be referred to by trade names including ETHILON®, MERSILENE®, PROLENE®, or other names. In a preferred embodiment, central wire 88 is made of nitinol, band 93 is made of platinum alloy, suture 94 is made of 7/0 (0.05 mm) PROLENE® monofilament suture, and band 93 is filled with medical grade epoxy.

Figure 8Q:
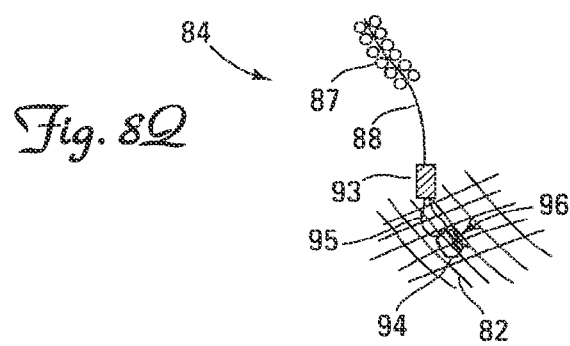
Figure 8R:
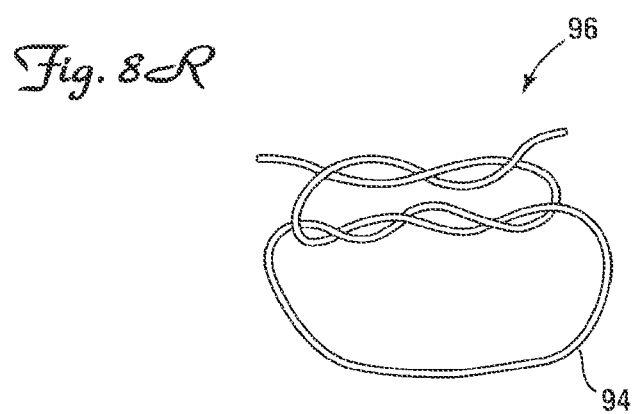

FIG. 8Q illustrates radiopaque element 84 having band 93, loop 95, central wire 88, coiled radiopaque wire 87 and flexible strand 94. Flexible strand 94 is used to attach loop 95 to mesh 82 by passing flexible strand through loop and through the thickness of mesh and then crimping, swaging, bonding, knotting or otherwise forming a closed loop from flexible strand 94. In a preferred embodiment, the ends of flexible strand 94 are tied in a knot 96, and knot 96 is a surgical knot such as the example illustrated in FIG. 8R.

Figure 8S:
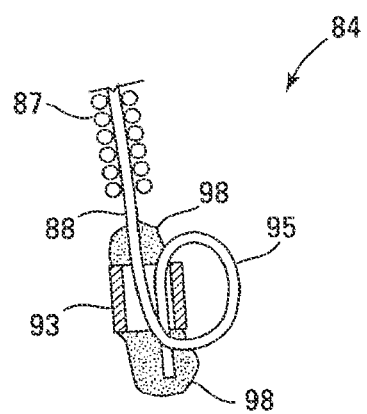
FIG. 8S illustrates conceptually a partial cross sectional view of a radiopaque element in accordance with the present invention.

In FIG. 8S radiopaque element 84 is positioned near opening 81 of mesh 82 and has one loop 95 and one band 93 at each end of element 84. In a preferred embodiment, each loop 95 encircles a portion of mesh 82 through the thickness of mesh 82 and central wire 88 passes through band 93 two times, each time in the same direction. Each band 93 is crimped to attach radiopaque element 84, and specifically central wire 88, to itself. Optionally, the end of coil 87 can also be crimped into band 93. Protective mass 98 may be comprised of adhesive, UV-curable adhesive, metallic solder or other materials. Mass 98 is applied to radiopaque element 84 at one or both ends of band 93 for the purpose of blunting end of central wire 88, band 93, and coil 87 and optionally for increasing retention of central wire 88 within band 93.

Figure 9:
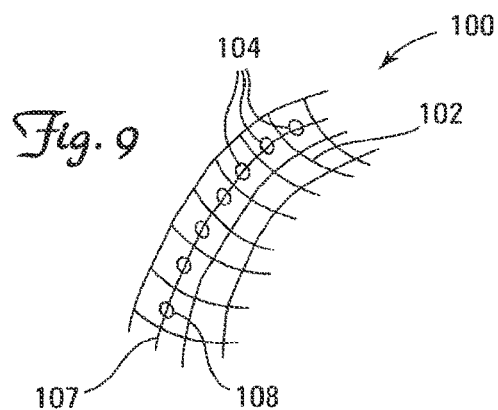
FIG. 9 illustrates conceptually a partial side view of an embolic protection device having radiopaque elements in accordance with the present invention.

FIG. 9 illustrates a mesh 102 of an embolic protective device 100 having radiopaque elements 104 in accordance with the present invention. To form the radiopaque elements 104, beads 108 of radiopaque material are attached to filament 107 of mesh 102. Beads 108 may be preformed and subsequently mechanically crimped onto filament 107, may comprise a through hole through which filament 107 is passed, may be applied over filament 107 in molten form and subsequently allowed to solidify, or may be attached to filament using other means known in the art. Filament 107 may be an interwoven portion of mesh 102, for example if the mesh is comprised of braided filaments, or may be applied to the mesh, for example if the mesh is comprised of polymer film having laser drilled holes.

Figure 9A:
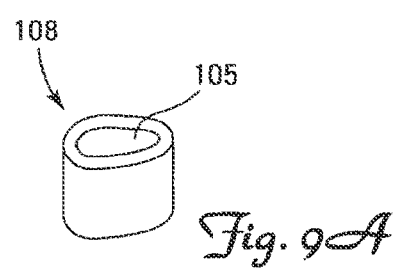
FIGS. 9A and 9D illustrate conceptually isometric views of radiopaque elements in accordance with the present invention.
Figure 9B:
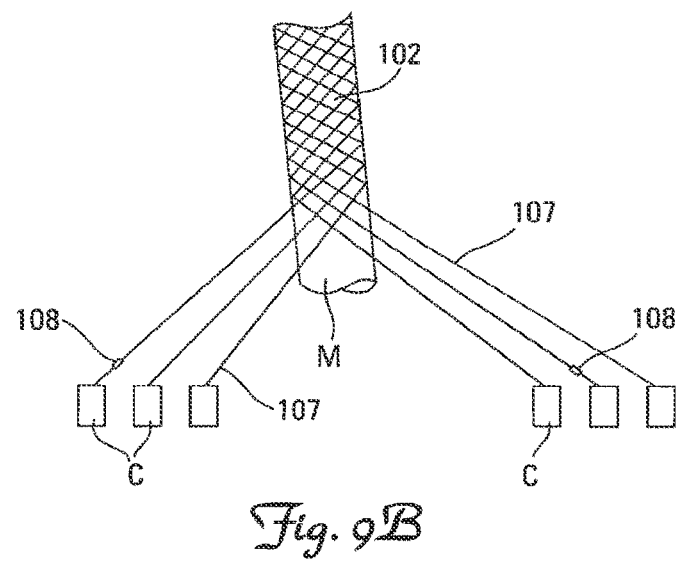
FIGS. 9B and 9C illustrate conceptually schematic side views of a manufacturing process for making an embolic protection device having radiopaque elements in accordance with the present invention.
Figure 9C:
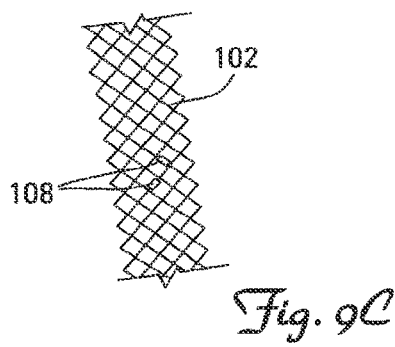
Figure 9D:
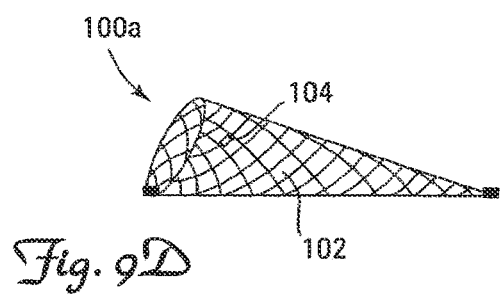

In an alternative embodiment, bead 108 is comprised of a tubular marker band applied to a mesh 102 during the manufacturing process. FIG. 9A illustrates bead 108 having a hollow cylinder shape, a lumen 105, and comprised of radiopaque material such as a platinum alloy. During manufacture of mesh 102, in the example of a braided mesh 102, one or more beads 108 are threaded onto one or more filaments 107 and beads 108 are positioned adjacent to carriers C prior to braiding filaments 107 onto mandrel M (FIG. 9B). After a length of mesh 102 has been braided, braiding is stopped, beads 108 are slid along filaments 107 to a position adjacent to mandrel M, and braiding is resumed. With this method, a length of mesh 102 is manufactured with beads 108 of radiopaque material applied to and integral with mesh 102 (FIG. 9C). Using techniques known in the art, mesh 102 can then be formed into an embolic protective device 100a having radiopaque elements 104 in accordance with the present invention (FIG. 9D).

FIGS. 10A and 10B illustrate an embolic protection device having radiopaque elements in accordance with the present invention. Embolic protection device 110 is comprised of mesh 112, radiopaque elements 114, and host wire 116 having tip (not shown). Mesh 112 is attached to proximal marker 118a and distal marker 118b. Proximal marker 118a and distal marker 118b slide relative to wire 116. Connector 119 limits the movement of proximal marker 118a and distal marker 118b. Radiopaque elements 114 comprise discontinuous loop segments extending around the perimeter of opening 111 of mesh 112 and having gaps 117. Radiopaque elements 114 are comprised of a coil configuration and are interwoven through the thickness of mesh 112, and may or may not be fixedly attached to mesh 112. Radiopaque elements 114 may extend around 5%, 10%, 20%, 30%, 40%, 50%, or any other percentage between 5% and 50% of the perimeter of opening 111, and 1, 2, 3, 4, 5, 6, 7, 8, 9, 10, or more radiopaque elements 114 may be applied to mesh 112. In a preferred embodiment, radiopaque elements 114 comprise gold plated tungsten wires coiled around the thickness of mesh 112 at the perimeter of opening 111, extending around 10% of the perimeter of opening Ill, and two radiopaque elements are applied to mesh 112.

FIGS. 11A and 11B illustrate an embolic protection device having radiopaque elements in accordance with the present invention. Embolic protection device 120 is comprised of mesh 122, radiopaque elements 124, and host wire 126 having tip (not shown). Mesh 122 is attached to proximal marker 128a and distal marker 128b. Proximal marker 128a and distal marker 128b slide relative to wire 126. Connector 120 limits the movement of proximal marker 128a and distal marker 128b. Radiopaque element 124 comprises discontinuous loop segments extending around perimeter of opening 121 of mesh 122 and having gaps 127. Radiopaque element 124 may extend around the inner diameter of mesh 122, external to the diameter of mesh 122, or may be interwoven through the thickness of mesh 122, and may or may not be fixedly attached to mesh 122. Radiopaque elements 124 may extend around 5%, 10%, 20%, 30%, 40%, 50%, or any other percentage between 5% and 50% of the perimeter of opening 121, and 1, 2, 3, 4, 5, 6, 7, 8, 9, 10, or more radiopaque elements 124 may be applied to mesh 122. In a preferred embodiment, radiopaque elements 124 comprise gold-plated tungsten wires interwoven through the thickness of mesh 122 at the perimeter of opening 121, extending around 10% of the perimeter of opening 121, and two radiopaque elements are applied to mesh 122.

FIGS. 11C to 11H, 11J, and 11K illustrate radiopaque elements in accordance with the present invention. FIG. 11 C illustrates radiopaque element 124 comprised of wire 131 and coils 132. Wire 131 and coil 132 may be attached using methods such as welding or adhesive bonding. Coil 132 is wrapped around wire 132 and through thickness of mesh 122 and optionally is secured to the mesh using adhesives or other attachment methods known in the art. In a preferred embodiment, wire 132 is made of platinum, 0.002" (0.0051 cm) in diameter and traverses 15% of the perimeter of the opening in filter 120, and the coils are comprised of 5 turns of platinum wire of 0.001" (0.0025 cm) diameter.

FIGS. 11D and 11E illustrate radiopaque element 124 comprised of wire 131 and crimp band 133. Wire 131 and crimp band 133 may be attached using methods such as welding or adhesive bonding. Crimp band 133 is crimped around wire 131 and through thickness of mesh 122 and optionally is secured to the mesh using adhesives or other attachment methods known in the art. In a preferred embodiment, wire 131 is made of platinum, 0.002" (0.0051 cm) in diameter and traverses 15% of the perimeter of the opening in filter 120, and the crimp bands are comprised of platinum 0.005" (0.013 cm) in diameter and 0.030" (0.076 cm) long with a lumen large enough to admit both wire 131 and the thickness of mesh 132. In an alternative embodiment, the crimp band is made of platinum 0.005" (0.013 cm) in diameter and 0.030" (0.076 cm) long with two lumens, one large enough to admit wire 131 and the other large enough to attach the thickness of mesh 122 (FIG. 11E).

FIG. 11F illustrates radiopaque element 124 comprised of wire 131 and curled ends 139. Wire 131 is attached though thickness of mesh 122 by curling end 139 of wire 131 through the mesh thickness and back onto itself. Optionally wire 131 is secured to itself using adhesives, solders, or other attachment methods known in the art. In a preferred embodiment, wire 131 is made of platinum, 0.002" (0.0051 cm) in diameter and traverses 15% of the perimeter of the opening in filter 120, and is silver soldered to itself in the vicinity of curled end 139.

FIG. 11G illustrates radiopaque element 124 comprised of wire 131 and attachment region 138. Wire 131 is attached to itself at attachment region 138 using methods such as welding, soldering, or adhesive bonding or other attachment methods known in the art. A segment of wire 131 is passed through the thickness of mesh 122 and wire 131 ends are secured to each other at attachment region 138 to form a continuous unbroken loop of wire 131, thereby securing radiopaque element 124 to mesh 122. In a preferred embodiment, wire 131 is made of platinum, 0.002" (0.0051 cm) in diameter and traverses 15% of the perimeter of the opening in filter 120, passes through the thickness of mesh 122 in two places, and is attached to itself at attachment region 138 using silver soldering.

FIGS. 11H, 11J and 11K illustrate radiopaque elements 124 comprised of stranded wire 137 twisted into filaments of mesh 122. To facilitate twisting around mesh filaments, central stranded wire 135 can be removed before stranded wire 137 is attached to mesh 122. Perimeter stranded wires 136 may be attached to each other using methods such as welding or adhesive bonding. In a preferred embodiment, stranded wire 137 is made of tungsten, 0.003" (0.0076 cm) in overall diameter, with one central strand and 6 perimeter strands, and traverses 15% of the perimeter of the opening in filter 120.

FIGS. 12A and 12B illustrate an embolic protection device having radiopaque elements in accordance with the present invention. Embolic protection device 140 is comprised of mesh 142, radiopaque elements 144, and host wire 146 having tip (not shown). Mesh 142 is attached to proximal marker 148a and distal marker 148b. Proximal marker 148a and distal marker 148b slide relative to wire 146. Connector 150 limits the movement of proximal marker 148a and distal marker 148b. Radiopaque element 144 comprises discontinuous elongate segments extending around the perimeter of opening 141 of mesh 142. Radiopaque elements 144 may extend along the inner diameter of mesh 142, external to diameter of mesh 142, or may be interwoven through the thickness of mesh 142, and may or may not be fixedly attached to mesh 142. Radiopaque elements 144 may extend along 5%, 10%, 20%, 30%, 40%, 50%, or any other percentage between 5% and 50% of the length of mesh 142, and 1, 2, 3, 4, 5, 6, 7, 8, 9, 10, or more radiopaque elements 144 may be applied to mesh 142. In a preferred embodiment, radiopaque elements 144 comprise gold-plated tungsten wires interwoven through the thickness of mesh 142 at the perimeter of opening 141, extending along 10% of the mesh length, and six radiopaque elements are applied to mesh 142.

Figure 13A:
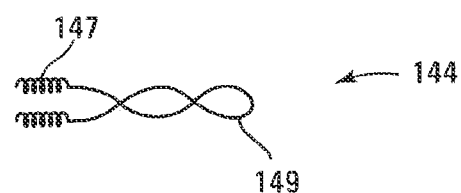
FIG. 13A to 13C illustrate conceptually side views of radiopaque elements in accordance with the present invention.
Figure 13B:
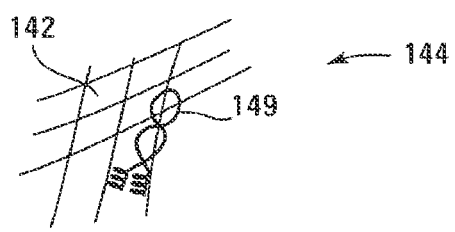
Figure 13C:
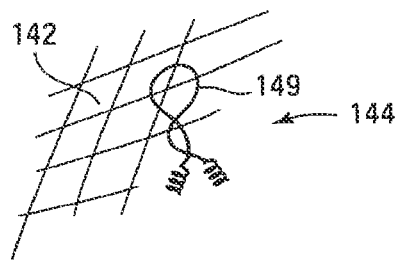

FIG. 13A to 13C illustrate radiopaque elements in accordance with the present invention. Radiopaque elements 144 are comprised of wire 149 twisted around through thickness of mesh 142. Twisted portions of wire 149 may be attached to each other using methods such as welding or adhesive bonding. Optionally, wire 149 comprises coiled ends 147 to facilitate both twisted end intertwinement and fluoroscopic visualization of wire 149. In a preferred embodiment, twisted wire 149 is made of platinum, 0.0015" (0.0038 cm) in diameter (untwisted), radiopaque element 144 extends along 15% of mesh length, and four radiopaque elements are applied to mesh 142. In an alternative embodiment, wire 149 is comprised of nitinol and heat set in a twisted configuration, and coiled ends 147 are made of platinum, radiopaque element 144 is passed through the thickness of mesh 142 and twisted nitinol wires 149 are intertwined to form a secure attachment to mesh 142 without use of adhesives, welding, soldering, or other joining techniques.

An illustrative method of using an embolic protection device having inventive radiopaque elements is as follows. Embolic protective device 60 is delivered percutaneously to a region of interest in the body of a patient using methods known in the art. Optionally a catheter is used to deliver the filter to the region of interest. Fluoroscopy is used by the operator to visualize the mouth of the filter to ascertain that the filter is positioned appropriately in relation to a treatment or diagnostic site, for example, positioned such that the mouth of the filter is distal to a stenosis in an artery, and also by example, positioned such that the body of the filter is in a healthy region of vessel suitable for use as a landing zone for the filter. The filter is then deployed and the catheter (if used) is removed from the vicinity of the filter. The operator uses fluoroscopy to ascertain that the mouth of the filter is adequately deployed against the vessel wall with no gaps, distal to the lesion, and proximal to any important side branch vessels. Radiopaque contrast media may be injected at this time or at any time to assist with visualization of the patient's anatomy. The treatment site is treated, for example, by dilating a lesion with a balloon dilatation catheter and by deploying a stent or drug eluting stent at the treatment site, although other methods known in the art can be used.

After or during treatment or both, the operator may visualize the mouth of the device and may adjust the position of the device to assure, for example, that the device is properly located along the length of the vessel and properly apposed to the vessel wall. After treatment the device is recovered. Optionally a catheter is used during the recovery process. At least a portion of the filter is drawn into the recovery catheter (if used) and the mouth of the filter is observed under fluoroscopy to ascertain when the device is sufficiently drawn into the catheter. If difficulty is encountered while drawing the filter into the catheter the devices are again imaged under fluoroscopy and the cause of the difficulty is diagnosed in part by observing the radiopaque portions of the device. The filter (and recovery catheter if used) are then withdrawn from the vessel. If resistance to withdrawal is encountered then the devices are imaged under fluoroscopy and the cause of resistance is determined and eliminated.

While this document has described an invention mainly in relation to radiopaque elements used for embolic protection filtering devices used in vessels, it is envisioned that the invention can be applied to other conduits in the body as well including veins, bronchi, ducts, ureters, urethra, and other lumens intended for the passage of air, fluids, or solids. The invention can be applied to other devices such as vena cava filters, stents, septal defect closure devices, intracranial filters, aneurism excluders, and stents, and other devices comprised of mesh having the benefits described above.

While the various embodiments of the present invention have related to embolic protection filtering devices, the scope of the present invention is not so limited. Further, while choices for materials and configurations have been described above with respect to certain embodiments, one of ordinary skill in the art will understand that the materials described and configurations are applicable across the embodiments.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A device comprising:
    a filter element comprising a mesh including a filament, the filter element being configured to expand from a collapsed configuration when the filter element is restrained to an expanded configuration when the filter element is unrestrained, wherein the filter element defines a cavity including a proximal facing opening in the expanded configuration;
    a bead of radiopaque material attached to the filament of the mesh;
    an elongate support member;
    a proximal marker disposed on the elongate support member and slideable with respect to the elongate support member; and
    a distal marker disposed on the elongate support member and slideable with respect to the elongate support member, wherein the mesh of the filter is attached to the proximal and distal markers,
    wherein the elongate support member comprises a stop between the proximal and distal markers that limits the movement of proximal and distal markers.

2. The device of claim 1, wherein the bead is mechanically crimped onto the filament.

3. The device of claim 1, wherein the bead defines a through hole through which the filament extends.

4. The device of claim 1, wherein the bead is formed over the filament.

5. The device of claim 1, wherein the bead comprises a tubular marker band.

6. The device of claim 1, wherein the bead comprises a plurality of beads.

7. The device of claim 1, wherein the radiopaque material comprises a platinum alloy.

8. The device of claim 1, wherein the filament comprises an interwoven portion of the mesh.

9. The device of claim 1, wherein the filament comprises a braided filament.

10. The device of claim 9, wherein the bead is integral with the braided filament.

11. The device of claim 1, wherein the mesh comprises a polymer film defining holes and the filament is applied to the polymer film.

12. A device comprising:
    a filter element comprising a mesh including a plurality of filaments braided together, the filter element being configured to expand from a collapsed configuration when the filter element is restrained to an expanded configuration when the filter element is unrestrained, wherein the filter element defines a cavity including a proximal facing opening in the expanded configuration;
    a plurality of beads of radiopaque material, each bead being threaded onto one or more filaments of the mesh and incorporated into the mesh; and
    an elongate support member, the filter element being carried on a portion of the elongate support member.

13. The device of claim 12, further comprising:
    a proximal marker disposed on the elongate support member and slideable with respect to the elongate support member; and
    a distal marker disposed on the elongate support member and slideable with respect to the elongate support member, wherein the mesh of the filter is attached to the proximal and distal markers,
    wherein the elongate support member comprises a stop between the proximal and distal markers that limits the movement of proximal and distal marker.

14. The device of claim 12, wherein the plurality of filaments are metal filaments.

15. A method comprising:
    forming a filter element comprising a mesh including a filament, the filter element being configured to expand from a collapsed configuration when the filter element is restrained to an expanded configuration when the filter element is unrestrained, wherein the filter element defines a cavity including a proximal facing opening in the expanded configuration; and
    attaching a bead of radiopaque material to the filament of the mesh,
    wherein the mesh of the filter element is configured to be attached to proximal and distal markers each disposed on an elongate support member and slideable with respect to the elongate support member, the elongate support member comprising a stop between the proximal and distal markers configured to limit the movement of proximal and distal markers.

16. The method of claim 15, wherein the mesh comprises a plurality of filaments braided together, and wherein attaching the bead to the filter comprises threading the bead onto at least one filament during braiding of the filaments.

17. The method of claim 16, wherein threading the bead onto at least one filament during braiding of the filaments comprises:
    braiding the filaments to define a first length of the mesh;
    sliding the bead along at least one filament to a position adjacent the first length of the mesh; and
    resuming the braiding of filaments to define a second length of the mesh, wherein the bead is positioned between the first and second lengths of the mesh.

18. The method of claim 15, wherein attaching the bead to the filament comprises mechanically crimping the bead to the filament.

19. The method of claim 15, wherein attaching the bead to the filament comprises threading the filament through a through hole defined by the bead.

20. The method of claim 15, wherein attaching the bead to the filament comprises applying the radiopaque material over the filament in molten form and subsequently allowing the molten radiopaque material to solidify.

21. The method of claim 15, wherein attaching the bead to the filament comprises attaching a plurality of beads to the filament.

\* \* \* \* \*